US007674785B2

(12) United States Patent
Gavin et al.

(10) Patent No.: US 7,674,785 B2
(45) Date of Patent: Mar. 9, 2010

(54) TOPICAL ANTI-MICROBIAL COMPOSITIONS

(75) Inventors: David Francis Gavin, Cheshire, CT (US); Anthony Raymond Marchetta, Mason, OH (US); John Daniel Nelson, Jr., Bethlehem, CT (US); George Polson, Harwinton, CT (US); James Robert Schwartz, West Chester, OH (US); Patricia Aileen Turley, Orange, CT (US)

(73) Assignees: The Procter & Gamble Company, Cincinnati, OH (US); Arch Chemicals, Inc., Norwalk, CT (US)

( * ) Notice: Subject to any disclaimer, the term of this patent is extended or adjusted under 35 U.S.C. 154(b) by 0 days.

(21) Appl. No.: 11/299,195

(22) Filed: Dec. 8, 2005

(65) Prior Publication Data

US 2006/0089342 A1    Apr. 27, 2006

Related U.S. Application Data

(62) Division of application No. 09/599,624, filed on Jun. 22, 2000, now Pat. No. 7,026,308.

(51) Int. Cl.
*A01N 55/02* (2006.01)

(52) U.S. Cl. ............................ 514/188; 424/59; 424/61; 424/70.27; 424/401; 424/405; 514/335; 514/345; 514/880; 514/881

(58) Field of Classification Search .................. None
See application file for complete search history.

(56) References Cited

U.S. PATENT DOCUMENTS

| 2,396,278 A | 3/1946 | Lind |
| 2,438,091 A | 3/1948 | Lynch |
| 2,486,922 A | 11/1949 | Strain |
| 2,488,921 A | 11/1949 | Byerly |
| 2,520,376 A | 10/1950 | Mannheimer |
| 2,658,072 A | 11/1953 | Kosmin |
| 2,694,668 A | 11/1954 | Fricke |
| 2,786,847 A | 3/1957 | Cislak |
| 2,798,053 A | 7/1957 | Brown |
| 2,809,971 A | 10/1957 | Bernstein |
| 2,826,551 A | 3/1958 | Geen |
| 2,951,789 A | 9/1960 | McCants |
| 3,152,048 A | 10/1964 | Kapral |
| 3,155,591 A | 11/1964 | Hilfer |
| 3,236,733 A | 2/1966 | Karsten |
| 3,326,733 A | 6/1967 | Colegrove |
| 3,332,880 A | 7/1967 | Kessler |
| 3,589,999 A | 6/1971 | McRae |
| 3,590,035 A | 6/1971 | Damico |
| 3,753,196 A | 8/1973 | Kurtz |
| 3,761,418 A | 9/1973 | Parran |
| 3,773,770 A | 11/1973 | Damico |
| 3,852,441 A | 12/1974 | Kooistra, Jr. |
| 3,929,678 A | 12/1975 | Laughlin |
| 3,940,482 A | 2/1976 | Grand |
| 3,958,581 A | 5/1976 | Abegg et al. |
| 3,959,461 A | 5/1976 | Bailey |
| 3,960,782 A | 6/1976 | Daley et al. |
| 3,964,500 A | 6/1976 | Drakoff |
| 4,055,655 A | 10/1977 | Maurer et al. |
| 4,089,945 A | 5/1978 | Brinkman |
| 4,152,416 A | 5/1979 | Spitzer |
| 4,161,526 A | 7/1979 | Gorman |
| 4,197,865 A | 4/1980 | Jacquet |
| 4,217,914 A | 8/1980 | Jacquet |
| 4,235,873 A | 11/1980 | Packman |
| 4,323,683 A | 4/1982 | Bolich |
| 4,345,080 A | 8/1982 | Bolich |
| 4,364,387 A | 12/1982 | Larkin |
| 4,370,325 A | 1/1983 | Packman |
| 4,374,852 A | 2/1983 | Hilditch et al. |
| 4,379,753 A | 4/1983 | Bolich |
| 4,381,919 A | 5/1983 | Jacquet |
| 4,387,090 A | 6/1983 | Bolich |
| 4,422,853 A | 12/1983 | Jacquet |
| 4,454,153 A | 6/1984 | Lowicki et al. |
| 4,470,982 A | 9/1984 | Winkler |
| 4,507,280 A | 3/1985 | Pohl |
| 4,529,586 A | 7/1985 | De Marco |
| 4,608,183 A | 8/1986 | Rossmoore |
| 4,654,213 A | 3/1987 | Ramirez |
| 4,663,158 A | 5/1987 | Wolfram |
| 4,666,616 A | 5/1987 | Rossmoore |
| 4,670,430 A | 6/1987 | Imamura |
| 4,686,254 A | 8/1987 | Lochhead |
| 4,704,272 A | 11/1987 | Oh |
| 4,788,006 A | 11/1988 | Bolich |
| 4,834,767 A | 5/1989 | Helioff |
| 4,885,107 A | 12/1989 | Wetzel |
| 4,898,585 A | 2/1990 | Borsanyi |
| 4,933,101 A | 6/1990 | Cilley et al. |

(Continued)

FOREIGN PATENT DOCUMENTS

CA    1264671    1/1990

(Continued)

OTHER PUBLICATIONS

Saxton, Charles A. et al. "Antiplaque effects and made of action of a combination of zinc citrate and a nonionic antimicrobial agent", *Scandinavian Journal of Dental Research*, Jun. 1988, p. 212-217, vol. 96, No. 3, XP-001079620, Copenhagen, Denmark.

(Continued)

*Primary Examiner*—Neil Levy
(74) *Attorney, Agent, or Firm*—Linda M. Sivik

(57) ABSTRACT

Disclosed are topical compositions for the treatment of microbial infections on the skin or scalp which include a polyvalent metal salt of pyrithione and include a metal ion source. Also disclosed are methods for treating microbial infections of the skin or scalp using such compositions.

16 Claims, No Drawings

U.S. PATENT DOCUMENTS

| | | | |
|---|---|---|---|
| 4,943,432 | A | 7/1990 | Biener |
| 5,057,153 | A | 10/1991 | Ruggiero |
| 5,104,645 | A | 4/1992 | Cardin et al. |
| 5,104,646 | A | 4/1992 | Bolich |
| 5,106,609 | A | 4/1992 | Bolich |
| 5,120,831 | A | 6/1992 | Pickart |
| 5,202,048 | A | 4/1993 | Bartolo et al. |
| 5,227,156 | A | 7/1993 | Wiese |
| 5,246,489 | A | 9/1993 | Farmer |
| 5,284,649 | A | 2/1994 | Juneja |
| RE34,584 | E | 4/1994 | Grote |
| 5,462,589 | A | 10/1995 | Nicholas |
| 5,478,501 | A | 12/1995 | Rau |
| 5,518,774 | A | 5/1996 | Kappock et al. |
| 5,540,954 | A | 7/1996 | Nicholas |
| 5,562,995 | A | 10/1996 | Kappock |
| 5,580,494 | A | 12/1996 | Sandhu et al. |
| 5,614,538 | A | 3/1997 | Nelson, Jr. |
| 5,674,478 | A | 10/1997 | Dodd |
| 5,696,169 | A | 12/1997 | Arima et al. |
| 5,723,112 | A | 3/1998 | Bowser et al. |
| 5,750,122 | A | 5/1998 | Evans |
| 5,798,121 | A | 8/1998 | Cauwet |
| 5,837,661 | A | 11/1998 | Evans |
| 5,854,266 | A | 12/1998 | Nelson, Jr. |
| 5,854,319 | A | 12/1998 | O'Lenick |
| 5,874,476 | A | 2/1999 | Hsu |
| 5,880,076 | A | 3/1999 | Vermeer |
| 5,883,085 | A | 3/1999 | Blank et al. |
| 5,883,154 | A | 3/1999 | Kappock |
| 5,939,203 | A | 8/1999 | Kappock et al. |
| 5,965,515 | A | 10/1999 | Rau |
| 6,017,562 | A | 1/2000 | Kaufman et al. |
| 6,034,043 | A | 3/2000 | Fujiwara |
| 6,309,628 | B1 | 10/2001 | Ansmann |
| 6,333,040 | B1 | 12/2001 | Boyxen et al. |
| RE37,793 | E | 7/2002 | Domenico |
| 6,495,538 | B2 | 12/2002 | Fliss |
| 6,534,788 | B1 | 3/2003 | Yeo |
| 6,649,585 | B1 | 11/2003 | Daute et al. |
| 6,774,096 | B1 | 8/2004 | Paye |
| 6,908,912 | B2 | 6/2005 | Rioux et al. |
| 2003/0030042 | A1 | 2/2003 | Sawada et al. |
| 2003/0044471 | A1 | 3/2003 | Sakuma et al. |
| 2003/0119805 | A1 | 6/2003 | Fliss |
| 2003/0215522 | A1 | 11/2003 | Johnson et al. |
| 2004/0058855 | A1 | 3/2004 | Schwartz et al. |
| 2004/0167114 | A1 | 8/2004 | Fliss |
| 2004/0191331 | A1 | 9/2004 | Schwartz et al. |
| 2004/0213751 | A1 | 10/2004 | Schwartz et al. |
| 2004/0223941 | A1 | 11/2004 | Schwartz et al. |
| 2005/0202984 | A1 | 9/2005 | Schwartz et al. |
| 2006/0024381 | A1 | 2/2006 | Schwartz et al. |
| 2006/0045861 | A1 | 3/2006 | Bejger |
| 2006/0046943 | A1 | 3/2006 | Erazo-Majewicz |
| 2007/0128147 | A1 | 6/2007 | Schwartz et al. |

FOREIGN PATENT DOCUMENTS

| | | | |
|---|---|---|---|
| CA | 2132170 | A | 3/1996 |
| EP | 37318 | A1 | 10/1981 |
| EP | 0077630 | B1 | 4/1985 |
| EP | 0717981 | A1 | 6/1996 |
| EP | 0589047 | B1 | 6/1999 |
| EP | 1145707 | A1 | 10/2001 |
| EP | 1161869 | A | 12/2001 |
| FR | 2478467 | | 9/1981 |
| FR | 2593801 | A1 | 8/1987 |
| GB | 761171 | | 11/1956 |
| GB | 849433 | | 9/1960 |
| GB | 2141929 | A | 1/1985 |
| GB | 2230190 | A | 10/1990 |
| JP | 52 092881 | A | 8/1977 |
| JP | 60-174707 | A | 9/1985 |
| JP | 61-236708 | A | 10/1986 |
| JP | 6-9352 | | 1/1994 |
| JP | HEI 6-134227 | | 5/1994 |
| JP | 06256689 | | 9/1994 |
| JP | 62-96402 | | 10/1994 |
| JP | A-07-053369 | | 2/1995 |
| JP | HEI 7-118103 | | 5/1995 |
| JP | 9-175984 | | 7/1997 |
| JP | A-10-510290 | | 10/1998 |
| JP | A-10-328280 | | 12/1998 |
| JP | A-11-228368 | | 8/1999 |
| KR | 1997-010124 | | 3/1997 |
| KR | 010124 | A | 2/2000 |
| RO | 87800 | A | 8/1983 |
| WO | WO-94/10973 | A1 | 5/1994 |
| WO | WO-95/34524 | A1 | 12/1995 |
| WO | WO-96/10387 | A2 | 4/1996 |
| WO | WO-96/25913 | A | 8/1996 |
| WO | WO-98/06260 | A1 | 2/1998 |
| WO | WO-98/47372 | A1 | 10/1998 |
| WO | WO-99/21558 | A1 | 5/1999 |
| WO | WO-99/59540 | A1 | 11/1999 |
| WO | WO-00/06107 | A1 | 2/2000 |
| WO | WO-01/00021 | A | 1/2001 |
| WO | WO-01/00151 | A | 1/2001 |
| WO | WO-01/41727 | A1 | 6/2001 |
| WO | WO-01/51418 | A1 | 7/2001 |
| WO | WO-01/93817 | A1 | 12/2001 |
| WO | WO-02/32381 | A2 | 4/2002 |
| WO | WO-02/076422 | A1 | 10/2002 |
| WO | WO-02/080943 | A1 | 10/2002 |
| WO | WO-03/082229 | A1 | 10/2003 |
| WO | WO-03/088957 | A1 | 10/2003 |
| WO | WO-03/088965 | A1 | 10/2003 |

OTHER PUBLICATIONS

*Encyclopedia of Polymer Science and Engineering*, 1989, pp. 204-308. vol. 15, Second Edition, John Wiley & Sons, Inc.

D.J. Burgess, "Practical Analysis of Complex Coacervate Systems", *Journal Colloid and Interface Science*, Nov. 1990, pp. 227-238, vol. 140, No. 1, Academic Press, Inc.

*CTFA Cosmetic Ingredient Dictionary*, 1982, 3$^{rd}$ Edition, The Cosmetic, Toiletry, and Fragrance Association, Inc., Washington, D.C. (book not enclosed).

Van Oss, C.J., "Coacervation, Complex-Coacervation and Flocculation", *J. Dispersion Science and Technology*, 1989, pp. 561-573, vol. 9 (5,6), Marcel Dekker, Inc.

Noll, Walter, *Chemistry and Technology of Silicones*, 1968, Academic Press, Inc., New York, NY. (book not enclosed).

McCutcheon, *Emulsifiers and Detergents*, 1989, MC Pub Co. (book not enclosed).

BASF, "Z-Cote microfine zinc oxide", XP-002287832, 2000, p. 1-7.

Van Cutsem, J. et al, XP-002288119, *Journal of the American Academy of Dermatology*, 1998, vol. 22, No. 61, p. 993-998, Amsterdam.

Bennett, E.O. et al. "The Effects of Metals Upon The Inhibitory Activities of Cutting Fluid Preservatives", *International Biodeterioration Bulletin*, ISSN 0020-6164 18(1) Spring 1982.

Akiyama, Hisanori, et al., "Effects of Zinc Oxide on the attachment of *Staphylococcus aureus* strains", *Journal of Dermatological Science*, 17 (1998) pp. 67-74.

MSDS Mallinckrodt Baker, Inc. Zinc Carbonate Feb. 16, 2006 pp. 1-7.

Hwang, Sung-Ho, et al., Intercalation of Functional Organic Molecules with Pharmaceutial, Cosmeutical and Nutraceutical Functions into Layered Double Hydroxides and Zinc Basic Salts.

Louer et al., Chemistry of Materials, 1998, 10, 2450-2461.

Kravzov et al.; Journal of Applied Toxicology, 1993, 13(3), 213-216, Abstract Only.

McMurray, John, Organic Chemistry, 2nd Edition, Brooks-Cole Publishing Company, p. 1010 (1988).

Khattar, M.M. and Salt, W.G., "Aspects of the Mode of Action of Pyrithione Against Klebsiela Pneumoniae," Journal of Antimicrobial Chemotherapy, 1993, 5(S1), pp. 175-177.

The Mineral Willemite [online] retrieved from the internet on Nov. 26, 2007 retrieved from: http://www.galleries.com/minerals/silicate/willemit/willemit.htm 2 pages.

Willemite [online] retrieved from the internet http://www.mindat.org/min-4292.html retrieved on Nov. 26, 2007; pp. 1-16.

US 7,674,785 B2

TOPICAL ANTI-MICROBIAL COMPOSITIONS

CROSS-REFERENCE TO RELATED APPLICATION

This Application is a Divisional Application of U.S. Ser. No. 09/599,624, Case Number 8135&, filed Jun. 22, 2000 now U.S. Pat. No. 7,026,308.

FIELD OF THE INVENTION

The present invention relates to topical anti-microbial compositions and methods of treating microbial infections on the skin or scalp. Of specific concern are methods for the treatment of dandruff and compositions which provide improved anti-dandruff activity. In particular, the present invention relates to methods and compositions utilizing a polyvalent metal salt of pyrithione and a metal ion source.

BACKGROUND OF THE INVENTION

Various anti-dandruff compositions are commercially available or otherwise known in the shampoo art. These compositions typically comprise detersive surfactants and particulate, crystalline anti-microbial agents dispersed and suspended throughout the composition. Anti-microbial agents used for this purpose include sulfur, selenium sulfide and polyvalent metal salts of pyridinethione. During the shampooing process, these anti-microbial agents deposit on the scalp to provide anti-dandruff activity. Soluble anti-dandruff agents, such as ketoconazole, are also known in the art.

Nevertheless, consumers desire an anti-dandruff shampoo which provides superior anti-dandruff efficacy.

Polyvalent metal salts of pyrithione (also known as 1-hydroxy-2-pyridinethione; 2-pyridinethiol-1-oxide; 2-pyridinethione; 2-mercaptopyridine-N-oxide; pyridinethione; and pyridinethione-N-oxide) are known to be effective biocidal agents and are widely used as fungicides and bacteriocides in paints and metalworking fluids. Polyvalent metal salts of pyrithione are also used as fungicides and bacteriocides in personal care compositions such as foot powders and anti-dandruff shampoos. The polyvalent metal salts of pyrithione are only sparingly soluble in water and include magnesium pyrithione, barium pyrithione, bismuth pyrithione, strontium pyrithione, copper pyrithione, zinc pyrithione, cadmium pyrithione, and zirconium pyrithione.

Zinc and copper pyrithione are especially useful as anti-microbial agents in personal care compositions. Zinc pyrithione is known as an anti-dandruff component in shampoos. Synthesis of polyvalent pyrithione salts is described in U.S. Pat. No. 2,809,971 to Berstein, et al. Other patents disclosing similar compounds and processes for making them include U.S. Pat. Nos. 2,786,847; 3,589,999; 3,590,035; and 3,773,770.

While pyrithione biocides have proven useful for a wide range of applications, the utility of these compounds is limited to the control of select species and strains of fungi and bacteria. Further, while higher concentrations of pyrithione salts have been observed to control the growth of a wider range of organisms, the useful amount of polyvalent metal salts of pyrithione that can be added to a commercial product is limited by efficacy and economic considerations, and environmental concerns. In personal care compositions, such as shampoos, the amounts of pyrithione salts that may be added is further limited by toxicological concerns.

Generally, the use of anti-microbial agents in anti-dandruff shampoos is also known in the art. However, although polyvalent metal salts of pyrithiones have been disclosed as anti-microbial and/or anti-dandruff agents, the overall efficacy has remained relatively low. Therefore, consumers desire a shampoo which provides superior anti-dandruff efficacy versus currently marketed products. Such a superior efficacy can be difficult to achieve.

For example, it was previously believed that anti-dandruff efficacy could be achieved by "solubilizing" a zinc pyrithione complex in a strong chelating agent. One such approach, disclosed in European Patent Application No. 077,630 to Dixon was to "solubilize" zinc pyrithione in a strong chelating agent in the presence of divalent copper cations. However, the "solubilization" process disclosed in the '630 application actually results in the break down of the chemical structure of the pyrithione complex. The resulting composition contains a complex of the chelating agent/zinc in solution with free pyrithione ions. The free pyrithione ions are soluble in the composition. The '630 application discloses that this approach results in a clear product that is physically stable and provides anti-dandruff benefits.

Unfortunately, the downside risk to this approach is that excessive amounts of the soluble free pyrithione ions are known to be toxic to humans and the use of such a composition would fall outside of the current Federal Drug Administration monograph for zinc pyrithione, making the composition commercially unacceptable for personal care products.

Metal ions, such as copper salts are also taught in the art to provide efficacy in anti-microbial applications. Copper compounds, such as copper sulfate and cuprous oxide have been used widely as fungicides, antifoulants, and algaecides in a large range of applications including paints, swimming pool water, and wood products. Similarly, inorganic salts of zinc such as zinc chloride, zinc sulfate, and zinc oxide have been employed as bacteriostatic and/or fungistatic compounds in a large variety of products including paints, coatings, and antiseptics. However, copper salts and zinc salts do not possess as high a level of biocidal efficacy as might be desired for many anti-dandruff and skin care applications.

It has now surprisingly been found, in accordance with the present invention, that anti-dandruff efficacy can be dramatically increased in topical compositions by the use of polyvalent metal salts of pyrithione, such as zinc pyrithione, in combination with a metal ion source such as copper and zinc salts. It is therefore an object of the present invention to provide an anti-dandruff topical composition with improved efficacy. The improved efficacy also allows for the reduction of the levels of metal pyrithiones in anti-microbial compositions, thereby facilitating the production of safer products containing anti-microbial actives.

It is an object of the present invention to provide topical skin and/or hair compositions which provide superior anti-dandruff efficacy. It is also an object of the present invention to provide a method for cleansing the hair and/or skin. It is also an object of the present invention to provide a method for treating athlete's foot. These, and other objects, will become readily apparent from the detailed description below.

SUMMARY OF THE INVENTION

The present invention relates to topical compositions for treating microbes, in order to inhibit or prevent the growth thereof, on the skin or scalp comprising: a) from about 0.001% to about 10%, by weight of the composition, of an anti-microbial active selected from the group consisting of polyvalent metal salts of pyrithione; b) from about 0.001% to about 10%, by weight of the composition, of a metal ion source selected from group consisting of zinc salts, copper salts, silver salts, nickel salts, cadmium salts, mercury salts, bismuth salts, and mixtures thereof, and c) a topical carrier for the anti-microbial active and the metal salt, wherein the weight ratio of the metal source to the anti-microbial active is from about 5:100 to about 5:1 and wherein at least 50% of the anti-microbial active is insoluble in the composition.

The present invention further relates to a method for providing anti-dandruff efficacy comprising applying to the hair and scalp an amount of the above-described composition which is effective to provide such benefits.

DETAILED DESCRIPTION OF THE INVENTION

The topical anti-dandruff compositions of the present invention can comprise, consist of, or consist essentially of the essential elements and limitations of the invention described herein, as well any of the additional or optional ingredients, components, or limitations described herein.

Particularly, these compositions comprise an anti-microbial agent, a metal ion source, and a topical carrier. Upon introduction of the anti-microbial particulate into the carrier, the anti-microbial particulate is incorporated therein, in the form of a dispersion, suspension, or emulsion, in the composition. The metal ion source then enhances the biocidal effect of the anti-microbial particulate.

All percentages, parts and ratios are based upon the total weight of the shampoo compositions of the present invention, unless otherwise specified. All such weights as they pertain to listed ingredients are based on the active level and, therefore, do not include carriers or by-products that may be included in commercially available materials.

The components, including those which may optionally be added, of the topical anti-microbial compositions of the present invention, as well as methods for preparation, and methods for use, are described in detail below.

A. Anti-Microbial Agent

The topical anti-microbial compositions of the present invention comprise from about 0.001% to about 10% of the anti-microbial agent. Preferably, the compositions comprise from about 0.01% to about 5%, more preferably from about 0.1% to about 2% of the anti-microbial agent.

The anti-microbial agent may be selected from polyvalent metal salts of pyrithione and mixtures thereof. Any form of polyvalent metal pyrithione salts may be used, including platelet and needle structures. Preferred salts for use herein include those formed from the polyvalent metals magnesium, barium, bismuth, strontium, copper, zinc, cadmium, zirconium and mixtures thereof, more preferably zinc. Even more preferred for use herein is the zinc salt of 1-hydroxy-2-pyridinethione (known as "zinc pyrithione" or "ZPT"), most preferably ZPT in platelet particle form, wherein the particles have an average size of up to about 20µ, preferably up to about 5µ, most preferably up to about 2.5µ.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, all of which are incorporated herein by reference.

It is further contemplated that when ZPT is used as the anti-microbial particulate in the anti-microbial compositions herein, that the growth or re-growth of hair may be stimulated or regulated, or both, or that hair loss may be reduced or inhibited, or that hair may appear thicker or fuller.

Zinc pyrithione may be made by reacting 1-hydroxy-2-pyridinethione (i.e., pyrithione acid) or a soluble salt thereof with a zinc salt (e.g. zinc sulfate) to form a zinc pyrithione precipitate, as illustrated in U.S. Pat. No. 2,809,971, incorporated herein by reference.

At least 50%; preferably at least 75%; more preferably at least 99.9%, even more preferably at least 99.99%, and still more preferably 100% of the polyvalent metal salt of pyrithione remains insoluble in the composition.

Preferably, less than 50%, more preferably less than 30%, more preferably less than 15%, more preferably less than 10%, more preferably less than 5%, even more preferably less than 1%, still more preferably 0%, of the polyvalent metal salt of pyrithione disassociates into free pyrithione ion in the composition. By "free pyrithione ion" as used herein, is meant soluble pyrithione ion that is not associated with polyvalent metal ions.

Preferably, the composition comprises at least a 5 to 1 ratio of polyvalent metal salt of pyrithione to strong chelating agents. Strong chelating agents include such compounds as di- or polyamines such as ethylene diamine tetra-acetic acid (EDTA), diethylene triamine penta-acetic acid (DTPA), tetraethylene triamine (TET), ethylene diamine (EDA) and diethylene triamine (DETA) or salts thereof. These chelating agents may be present in relatively small amounts, i.e. less than 1%, preferably less than 0.5%, more preferably less than 0.1%, by weight of the composition, when used as preservatives or metal stabilizers. Preferably, the composition is free of strong chelating agents.

B. Metal Ion Source

The topical anti-microbial compositions of the present invention comprise from about 0.001% to about 10% of the metal ion source. Preferably, the compositions of the present invention comprise from about 0.01% to about 5%, more preferably from about 0.1% to about 2% of the metal ion source.

The metal ion source may be selected from zinc, copper, silver, nickel, cadmium, mercury, and bismuth. Preferably, the metal ion is selected from zinc salts, copper salts, silver salts, and mixtures thereof. More preferably the metal ion is selected from zinc salts, copper salts, and mixtures thereof.

Examples of zinc salts that may be used in the compositions of the present invention include zinc acetate, zinc oxide, zinc carbonate, zinc hydroxide, zinc chloride, zinc sulfate, zinc citrate, zinc fluoride, zinc iodide, zinc lactate, zinc oleate, zinc oxalate, zinc phosphate, zinc propionate, zinc salicylate, zinc selenate, zinc silicate, zinc stearate, zinc sulfide, zinc tannate, zinc tartrate, zinc valerate, zinc gluconate, zinc undecylate, and the like. Combinations of zinc salts may also be used in the composition of the invention.

Examples of suitable copper salts include copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, and the like. Combinations of these copper salts may also be used in the composition of the invention.

A variety of forms of silver may also be used. Examples of useful silver species include colloidal silver, silver salts, and silver complexes, such as silver bromide, silver chloride, silver citrate, silver iodide, silver lactate, silver nitrate, silver oxide, silver picrate, and the like.

In addition, combinations of metal salts may also be used in the composition of the invention.

The metal ion source is present in the composition at a ratio to polyvalent metal salt of pyrithione of from about 5:100 to about 5:1; preferably from about 2:10 to about 3:1; more preferably from about 1:2 to 2:1.

C. Topical Carrier

The topical anti-microbial compositions of the present invention include a topical carrier. The topical carrier may be selected from a broad range of traditional personal care carriers depending on the type of composition to be formed. By suitable selections of compatible carriers, it is contemplated that the present anti-microbial compositions may be prepared in the form of daily skin or hair products such as skin lotions or hair rinses, daily hair-grooming products, such as hair lotions, hair sprays, hair tonics, conditioning treatments and dressings, and the like, or they may be prepared in the form of cleansing products, such as hair and/or scalp shampoos, body washes, hand cleansers, water-less hand sanitizer/cleansers, and the like.

The topical carrier in liquid hair or skin compositions may be water, common organic solvents, or mixtures thereof. Suitable common organic solvents are C2-C3 lower monohydric or polyhydric alcohols such as ethanol, propanol, isopropanol, glycerine, dimethylformamide, dimethylacetamide, and dimethylsulfoxide.

In liquid cleansing compositions, such as shampoos, the carrier may include a detersive surfactant to provide cleaning performance to the composition. Such surfactants should be physically and chemically compatible with the essential components described herein, or should not otherwise unduly impair product stability, aesthetics, or performance. Examples of detersive surfactants useful herein are discussed below.

The anti-microbial compositions of the present invention may be aqueous systems which comprise from about 40% to about 92%, preferably from about 50% to about 85%, more preferably from about 60% to about 80%, water by weight of the compositions.

When the compositions of the present invention are an anti-dandruff shampoo, the pH of the compositions ranges, in general, from about 2 to about 10, preferably from about 3 to about 9, more preferably from about 4 to about 8, most preferably from about 5.5 to about 7.5.

The anti-microbial compositions of the present invention may also be in the form of a solid powder for application to the skin. Such a powder may comprise a solid cosmetic carrier. The solid cosmetic carrier may be talc, which is a hydrated magnesium silicate, used in the form of particles generally less than 40 μm in size; micas, which are aluminosilicates compositions, which exist in the form of scales which are 2 to 200 μm; modified or unmodified starch, in particular rice starch; silica; alumina; boron nitride; kaolin, which is a hydrated aluminum silicate; zinc and titanium oxides; precipitated calcium carbonate; magnesium carbonate or hydrocarbonate; metallic soaps derived from a carboxylic organic acid having 8 to 22 carbon atoms, for example zinc, magnesium or lithium stearate, zinc laurate, magnesium myristate and the like; synthetic polymer (or copolymer) powders chosen from polyethylene and its derivatives, for example polytetrafluoroethylene, polystyrene and the like; polyacrylates, polymethacrylates, polyesters or polyamides and the like, for example nylon powders; and powders in the form of hollow microspheres made from thermoplastic synthetic material, whose hollow part contains a gas.

1. Detersive Surfactant

The topical carrier component of the present invention may include a detersive surfactant selected from anionic surfactants, nonionic surfactants, amphoteric surfactants, zwitterionic surfactants, cationic surfactants and combinations thereof. A detersive surfactant provides an anti-microbial shampoo composition with cleaning performance. Any such surfactant known in the art for use in hair or personal care products may be used, provided that the surfactant is chemically and physically compatible with the essential components of the composition, or does not otherwise unduly impair product performance, aesthetics, or stability. The concentration of the surfactants in the shampoo composition may vary with the cleansing or lather performance desired, the particular surfactant selected, the desired product concentration, the presence of other components in the composition, and other factors well known in the art.

a) Anionic Surfactant

Suitable anionic surfactants for use herein include anionic detersive surfactants and zwitterionic or amphoteric detersive surfactant having an attached moiety that is anionic at the pH of the composition, or mixtures thereof. Preferred are anionic detersive surfactants. Such surfactants should be physically and chemically compatible with the essential components described herein, and should not otherwise unduly impair product stability, aesthetics or performance.

Examples of suitable anionic detersive surfactant components for use in the anti-microbial compositions herein include those which are known for use in hair care or other personal care cleansing compositions. The concentration of the anionic surfactant component in the composition should be sufficient to provide the desired cleaning and lather performance, and generally range from about 5% to about 50%, preferably from about 8% to about 30%, more preferably from about 10% to about 25%, even more preferably from about 12% to about 22%, by weight of the composition.

Preferred anionic surfactants suitable for use in the anti-microbial compositions herein are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic detersive surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Specific non limiting examples of alkyl ether sulfates which may be used in the anti-microbial compositions of the present invention include sodium and ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Specific examples of preferred alkyl sulfates include ammonium lauryl sulfate, ammonium cocoyl sulfate, potassium lauryl sulfate, potassium cocoyl sulfate, sodium lauryl sulfate, sodium cocoyl sulfate, monoethanolamine lauryl sulfate, monoethanolamine cocoyl sulfate, diethanolamine lauryl sulfate, triethanolamine lauryl sulfate, triethylamine lauryl sulfate, and mixtures thereof. Especially preferred is ammonium lauryl sulfate.

Specific examples of preferred alkyl ether sulfates include ammonium laureth sulfate, potassium laureth sulfate, sodium laureth sulfate, monoethanolamine laureth sulfate, diethanolamine laureth sulfate, triethanolamine laureth sulfate, triethylamine laureth sulfate, and mixtures thereof. Especially preferred is ammonium laureth sulfate.

Still another class of sulfate surfactants suitable for use in the for use in the anti-dandruff and conditioning shampoo embodiments of the present invention are the sulfated glycerides, an example of which includes lauric monoglyceride sodium sulfate.

Other suitable anionic detersive surfactants are the water-soluble salts of organic, sulfuric acid reaction products conforming to the formula $[R^1—SO_3-M]$ where $R^1$ is a straight or branched chain, saturated, aliphatic hydrocarbon radical having from about 8 to about 24, preferably about 10 to about 18, carbon atoms; and M is a cation described hereinbefore. Non limiting examples of such detersive surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. No. 2,486,921; U.S. Pat. No. 2,486,922; and U.S. Pat. No. 2,396,278, which descriptions are incorporated herein by reference.

Other anionic detersive surfactants suitable for use in the anti-microbial compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880, which description is incorporated herein by reference.

Another class of anionic detersive surfactants suitable for use in the anti-microbial compositions are the beta-alkyloxy alkane sulfonates. These surfactants conform to the formula

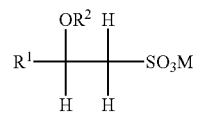

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Still other sulfonates suitable for use in the anti-microbial compositions of the present invention are those anionic detersive surfactants known as alkyl aryl sulfonates. Non-limiting examples of alkyl aryl sulfonates include sodium tridecyl benzene sulfonate, sodium dodecyl benzene sulfonate, and mixtures thereof.

Also suitable for use in the anti-microbial compositions of the present invention are those anionic detersive surfactants known as sarcosinates and sarcosine derivatives. Sarcosinates are the derivatives of sarcosine and N-methyl glycine, acylated with a fatty acid chloride. They conform to the general Formula (II):

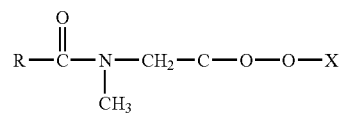

wherein RCO— is a fatty acid radical and wherein X is either hydrogen (acid form) or a cationic species, such as $Na^+$ or $TEA^+$ (salt form). Non-limiting examples of sarcosinates and sarcosine derivatives include: sodium lauryl sarcosinate, lauryl sarcosine, cocoyl sarcosine, and mixtures thereof. A preferred sarcosinate is sodium lauryl sarcosinate.

Preferred anionic detersive surfactants for use in the anti-microbial compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

b) Nonionic Surfactants

Nonionic surfactants suitable for use in compositions of the present invention may include condensation products of aliphatic primary or secondary linear or branched chain alcohols or phenols with alkylene oxides, usually ethylene oxide and generally having from 6 to 30 ethylene oxide groups. Other suitable nonionics include mono- or di-alkyl alkanolamides. Examples include coco mono- or di-ethanolamide and coco mono-isopropanolamide.

c) Amphoteric and Zwitterionic Surfactants

Suitable amphoteric or zwitterionic detersive surfactants for use in the shampoo composition herein include those which are known for use in hair care or other personal care cleansing. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.), which descriptions are incorporated herein by reference.

Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Commercially available amphoteric surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Zwitterionic detersive surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Preferred zwitterionic detersive surfactants are the betaines.

d) Cationic Surfactants

Cationic detersive surfactants suitable for use herein include surfactants containing quaternary nitrogen moieties. Examples of suitable cationic surfactants are those corresponding to the general Formula (XVIII):

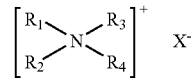

wherein $R_1$, $R_2$, $R_3$, and $R_4$ are independently selected from a $C_1$ to $C_{22}$ aliphatic group or an aromatic, alkoxy, polyoxyalkylene, alkylamido, hydroxyalkyl, aryl or alkylaryl group having up to about 22 carbon atoms, preferably $C_1$ to $C_{22}$ alkyl; and X is a salt-forming anion, such as those selected from halogen (e.g. chloride, bromide), acetate, citrate, lactate, glycolate, phosphate nitrate, sulfate, and alkylsulfate radicals. The aliphatic groups can contain, in addition to carbon and hydrogen atoms, ether linkages, and other groups, such as amino groups. The longer chain (e.g. $C_{12}$ and higher) aliphatic groups can be saturated or unsaturated.

Preferred cationic detersive surfactants are those containing two long alkyl chains and two short alkyl chains or those containing one long alkyl chain and three short alkyl chains. Such long alkyl chains are preferably from $C_{12}$ to $C_{22}$, more preferably from $C_{16}$ to $C_{22}$. Such short alkyl chains are preferably from $C_1$ to $C_3$, more preferably from $C_1$ to $C_2$.

Nonionic detersive surfactants suitable for use herein include, but are not limited to, those compounds produced by condensation of alkylene oxide groups (hydrophilic in nature) with an organic hydrophobic compound, which may be aliphatic or alkyl aromatic in nature.

Non-limiting examples of other anionic, nonionic, amphoteric, zwitterionic, and cationic detersive surfactants suitable for use in anti-microbial compositions of the present invention are described in McCutcheon's, Emulsifiers and Detergents, (1989), published by M. C. Pub. Co., and in U.S. Pat. No. 2,438,091; U.S. Pat. No. 2,528,378; U.S. Pat. No. 2,658,072; U.S. Pat. No. 3,155,591; U.S. Pat. No. 3,929,678; U.S. Pat. No. 3,959,461; U.S. Pat. No. 4,387,090; U.S. Pat. No. 5,104,646; U.S. Pat. No. 5,106,609; and U.S. Pat. No. 5,837,661, all of which descriptions are incorporated herein by reference.

2. Volatile Carrier

When the hair styling polymers described below are included in the anti-microbial compositions of the present invention, especially the hair styling shampoo embodiments, it is particularly preferable to also include a volatile carrier to solubilize the hair styling polymer. Such a carrier helps disperse the hair styling polymer as water-insoluble fluid particles throughout the composition, wherein the dispersed particles comprise the styling polymer and the volatile carrier. Carriers suitable for this purpose include hydrocarbons, ethers, esters, amines, alkyl alcohols, volatile silicone derivatives and combinations thereof, many examples of which are well known in the art.

Such a volatile carrier must be water-insoluble or have a low water solubility. The selected styling polymer, however, must also be sufficiently soluble in the selected carrier to allow dispersion of the hair styling polymer and solvent combination as a separate, dispersed fluid phase in the styling shampoo composition. The carrier used must also be volatile. In this context, the term volatile means that the carrier has a boiling point of less than about 300° C., preferably from about 90° C. to about 260° C., more preferably from about 100° C. to about 200° C. (at about one atmosphere of pressure).

The concentration of a volatile carrier in the composition must be sufficient to solubilize the hair styling polymer and disperse it as a separate fluid phase in the shampoo composition. Such concentrations generally range from about 0.10% to about 10%, preferably from about 0.5% to about 8%, most preferably from about 1% to about 6%, by weight of the shampoo composition, wherein the weight ratio of styling polymer to carrier is preferably from about 10:90 to about 70:30, more preferably from about 20:80 to about 65:35, even more preferably from about 30:70 to about 60:40. If the weight ratio of styling polymer to carrier is too low, the lathering performance of the shampoo composition will be negatively affected. If the ratio of polymer to solvent is too high, the composition becomes too viscous and causes difficulty in the dispersion of the styling polymer. The hair styling agents should have an average particle diameter in the final shampoo product of from about 0.05 to about 100 microns, preferably from about 1 to about 25 microns, more preferably from about 0.5 to about 10 microns. Particle size can be measured according to methods known in the art, including, for example optical microscopy.

Preferred volatile carriers for use in the shampoo composition are the hydrocarbon solvents, especially branched chain hydrocarbon solvents. The hydrocarbon solvents may be linear or branched, saturated or unsaturated, hydrocarbons having from about 8 to about 18 carbon atoms, preferably from about 10 to about 16 carbon atoms. Saturated hydrocarbons are preferred, as are branched hydrocarbons. Nonlimiting examples of some suitable linear hydrocarbons include decane, dodecane, decene, tridecene, and combinations thereof. Suitable branched hydrocarbons include isoparaffins, examples of which include commercially available isoparaffins from Exxon Chemical Company such as Isopar H and K ($C_{11}$-$C_{12}$ isoparaffins), and Isopar L ($C_{11}$-$C_{13}$ isoparaffins). Preferred branched hydrocarbons are isohexadecane, isododecane, 2,5-dimethyl decane, isotetradecane, and combinations thereof. Commercially available branched hydrocarbons include Permethyl 99A and 101A (available from Preperse, Inc., South Plainfield, N.J., USA).

Other suitable volatile carriers include isopropanol, butyl alcohol, amyl alcohol, phenyl ethanol, benzyl alcohol, phenyl propanol, ethyl butyrate, isopropyl butyrate, diethyl phthalate, diethyl malonate, diethyl succinate, dimethyl malonate, dimethyl succinate, phenyl ethyl dimethyl carbinol, ethyl-6-acetoxyhexanoate, and methyl (2-pentanyl-3-oxy)cyclopentylacetate, and mixtures thereof. Preferred among such other suitable solvents are diethyl phthalate, diethyl malonate, diethyl succinate, dimethyl malonate, dimethyl succinate, phenylethyl dimethyl carbinol, ethyl-6-acetoxyhexanoate, and mixtures thereof.

Suitable ether carriers are the di($C_5$-$C_7$) alkyl ethers and diethers, especially the di($C_5$-$C_6$) alkyl ethers such as isoamyl ether, dipentyl ether and dihexyl ether.

Other suitable volatile carriers for use in the anti-microbial compositions herein include the volatile silicon derivatives such as cyclic or linear polydialkylsiloxane, linear siloxy compounds or silane. The number of silicon atoms in the cyclic silicones is preferably from about 3 to about 7, more preferably about 3 to about 5.

The general formula for such silicones is:

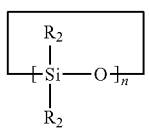

wherein $R_1$ and $R_2$ are independently selected from $C_1$ to $C_8$ alkyl, aryl or alkylaryl and wherein n=3-7. The linear polyorgano siloxanes have from about 2 to 7 silicon atoms and have the general formula:

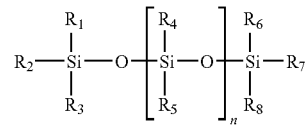

wherein $R_1$, $R_2$, $R_3$, $R_4$, $R_5$, $R_6$, $R_7$ and $R_8$ can independently be saturated or unsaturated $C_1$-$C_8$ alkyl, aryl, alkylaryl, hydroxyalkyl, amino alkyl or alkyl siloxy.

Linear siloxy compounds have the general formula:

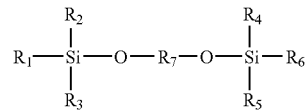

wherein $R_1$, $R_2$, $R_3$, $R_4$, $R_5$, and $R_6$ are independently selected from saturated or unsaturated $C_1$ to $C_7$ alkyl, aryl and alkyl aryl and $R_7$ is $C_1$ to $C_4$ alkylene.

Silane compounds have the general formula:

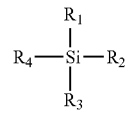

wherein $R_1$, $R_2$, $R_3$, and $R_4$ can independently be selected from $C_1$-$C_8$ alkyl, aryl, alkylaryl, hydroxyalkyl and alkylsiloxy.

Silicones of the above type, both cyclic and linear, are offered by Dow Corning Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes. Examples of volatile silicones are described in Todd and Byers, "Volatile Silicone Fluids for Cosmetics", Cosmetics and Toiletries, Vol. 91, January, 1976, pp. 27-32, and also in Silicon Compounds, pages 253-295, distributed by Petrarch Chemicals, which descriptions are incorporated herein by reference.

3. Select Stability Active

In the styling shampoo embodiments of the present invention that include a hair styling polymer and a volatile carrier, it is also preferable that the composition contain a select stability active. The select crystalline, hydroxyl-containing stabilizer is used to form a crystalline stabilizing network in the emulsion that prevents the styling polymer/volatile carrier droplets from coalescing and the shampoo from phase splitting. Additionally, significantly lower levels of the crystalline, hydroxyl-containing stabilizer need to be used relative to traditional stability actives. This results in enhanced deposition efficiency of the hair styling polymer onto the hair as well as reduced interactions with other shampoo components.

The stabilizer suitable for use in the shampoo compositions are characterized by the general formula:

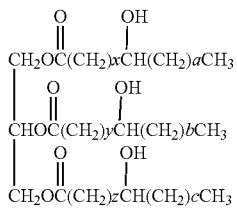

wherein:
(x+a) is from between 11 and 17,
(y+b) is from between 11 and 17,
(z+c) is from between 11 and 17;

preferably:
x=y=z=10, and
a=b=c=5.

The crystalline, hydroxyl-containing stabilizer comprises from about 0.005% to about 0.5%, preferably from about 0.05% to about 0.25% by weight of the composition. A preferred stabilizing agent for use in the styling shampoo embodiments of the anti-microbial compositions herein is trihydroxstearin available from Rheox, Inc. (New Jersey, USA) under the tradename "THIXCIN R."

Optional Ingredients

A. Other Anti-Microbial Actives

In addition to the anti-microbial active selected from polyvalent metal salts of pyrithione, the compositions of the present invention may further comprise one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox, compound undecylenic acid, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), and azoles. Preferred anti-microbials include itraconazole, ketoconazole, selenium sulphide and coal tar.

1. Azoles

Azole anti-microbials include imidazoles such as bironazole, butaconazole nitrate, climbazole, clotrimazole, croconazole, eberconazole, econazole, fenticonazole, flutimazole, isoconazole, itraconazole, ketoconazole, lanoconazole, miconazole, neticonazole, omoconazole, oxiconazole nitrate, sertaconazole, sulconazole nitrate, tioconazole, and trizoles such as terconazole. When present in the composition, the azole anti-microbial active is included in an amount from about 0.01% to about 5%, preferably from about 0.1% to about 3%, and more preferably from about 0.3% to about 2%, by weight of the composition. Especially preferred herein is ketoconazole.

2. Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), preferably less than 10 µm. Selenium sulfide compounds are described, for example, in U.S. Pat. No. 2,694,668; U.S. Pat. No. 3,152,046; U.S. Pat. No. 4,089,945; and U.S. Pat. No. 4,885,107, all of which descriptions are incorporated herein by reference.

3. Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

B. Suspending or Thickening Agent

The anti-microbial compositions of the present invention may, in some embodiments, comprise from about 0.1% to about 10%, by weight of the composition, preferably from about 0.3% to about 5%, more preferably from about 0.3% to about 2.5%, of a suspending agent suitable for application to the hair or skin. It is believed that the suspending agent suspends water-insoluble, dispersed materials in the anti-microbial compositions. Such suspending agent should be physically and chemically compatible with the essential components of the composition, and should not otherwise unduly impair product stability, aesthetics or performance. Examples of suspending agents which may be suitably employed in the anti-microbial compositions herein include, but are not limited to: acyl derivatives, long chain amine oxides, xanthan gum, and mixtures thereof. These and other suitable suspending agents are described in further detail below.

Crystalline suspending agents are preferred for suspending the particulate anti-microbial agent in the anti-microbial compositions. The selected suspending agent, at the selected concentration, should help maintain the suspension for at a period of at least one month, preferably at least three months, more preferably at least about twenty-four months, at ambient temperatures. In general, effective concentrations of the crystalline suspending agent range from about 0.5% to about 10%, preferably from about 0.5% to about 5%, more preferably about 1% to about 4%, most preferably about 1% to about 3%, by weight of the anti-microbial composition.

In general, concentrations of the crystalline suspending agent should be minimized to achieve only the desired property.

Preferred crystalline suspending agents are acyl derivatives and amine oxides, especially acyl derivatives, especially those which can be solubilized in a premix solution and then be recrystallized upon cooling. These materials comprise long chain (e.g., $C_8$-$C_{22}$ preferably $C_{14}$-$C_{22}$, more preferably $C_{16}$-$C_{22}$) aliphatic groups, i.e., long chain acyl derivative materials and long chain amine oxides, as well as mixtures of such materials. Included are ethylene glycol long chain esters, alkanol amides of long chain fatty acids, long chain esters of long chain fatty acids, glyceryl long chain esters, long chain esters of long chain alkanolamides, and long chain alkyl dimethyl amine oxides, and combinations thereof.

Crystalline suspending agents are described, for example, in U.S. Pat. No. 4,741,855, which description is incorporated herein by reference.

Suitable suspending agents for use in the anti-microbial compositions herein include ethylene glycol esters of fatty acids preferably having from about 14 to about 22 carbon atoms, more preferably 16-22 carbon atoms. More preferred are the ethylene glycol stearates, both mono and distearate, but particularly the distearate containing less than about 7% of the mono stearate. Other suspending agents include alkanol amides of fatty acids, preferably having from about 16 to about 22 carbon atoms, more preferably about 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate); glyceryl esters (e.g., glyceryl distearate) and long chain esters of long chain alkanol amides (e.g., stearamide diethanolamide distearate, stearamide monoethanolamide stearate). Ethylene glycol esters of long chain carboxylic acids, long chain amine oxides, and alkanol amides of long chain carboxylic acids, in addition to the preferred materials listed above, may be used as suspending agents.

Suspending agents also include long chain amine oxides such as alkyl ($C_{16}$-$C_{22}$) dimethyl amine oxides, e.g., stearyl dimethyl amine oxide.

Other long chain acyl derivatives that can be used include N,N-dihydrocarbyl ($C_{12}$-$C_{22}$, preferably $C_{16}$-$C_{18}$) amido benzoic acid and soluble salts thereof (e.g., Na and K salts), particularly N,N-di($C_{16}$-$C_{18}$, and hydrogenated tallow) amido benzoic acid species of this family, which are commercially available from Stepan Company (Northfield, Ill., USA).

The crystalline suspending agent can be incorporated into the anti-microbial compositions herein by solubilizing it into a solution containing water and an anionic sulfate surfactant at a temperature above the melting point of the suspending agent. The suspending agent is then recrystallized, typically by cooling the solution to a temperature sufficient to induce crystallization.

Other suitable suspending agents for use in the anti-microbial compositions that can be used include polymeric thickeners, such as carboxyvinyl polymers, examples of which are described in U.S. Pat. No. 2,798,053, and U.S. Pat. No. 4,686,254, which descriptions are incorporated herein by reference. Examples of suitable carboxyvinyl polymers include Carbopol®934, -940, -941, -956, -980, -981, -1342, and -1382, all commercially available from B.F. Goodrich Company.

Other suitable suspending agents include those which impart a gel-like viscosity to the composition, such as water soluble or colloidally water soluble polymers like cellulose ethers (e.g., hydroxyethyl cellulose), guar gum, polyvinyl alcohol, polyvinyl pyrrolidone, hydroxypropyl guar gum, starch and starch derivatives, and other thickeners, viscosity modifiers, gelling agents, xanthan gum and combinations thereof. A preferred viscosity modifier useful as a suspending agent is trihydroxystearin, (e.g. THIXIN R™, available from Rheox Company).

Other suitable suspending agents are described in U.S. Pat. Nos. 4,788,006 and 4,704,272 which descriptions are incorporated herein by reference.

C. Cationic Deposition Polymer

The anti-microbial compositions of the present invention may, in some embodiments, include an organic cationic polymer for use as a deposition aid. Such a deposition aid is especially useful in anti-microbial compositions which also contain a styling polymer as described hereinafter. When included in compositions of the present invention, the concentration of the cationic polymer ranges from about 0.025% to about 3%, preferably from about 0.05% to about 0.5%, more preferably from about 0.1% to about 0.25%, by weight of the composition.

Examples of suitable cationic polymers for use in the compositions of the present invention include cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. The average molecular weight of the cationic polymer is between about 10 million and about 5,000, preferably at least about 100,000, more preferably at least about 200,000, but preferably not more than about 2 million, more preferably not more than about 1.5 million. The polymers also have a cationic charge density ranging from about 0.2 meq/gm to about 7 meq/gm, preferably at least about 0.4 meq/gm, more preferably at least about 0.6 meq/gm, but also preferably less than about 5 meq/gm, more preferably less than about 2 meq/gm, at the pH of intended use of the composition, which for shampoo compositions, the pH will generally range from about pH 3 to about pH 9, preferably between about pH 4 and about pH 7.

Any anionic counterions can be used in association with the cationic polymers so long as the polymers remain soluble in water, in the composition, or in a coacervate phase of a shampoo composition, and so long as the counterions are physically and chemically compatible with the essential components of the composition or do not otherwise unduly impair product performance, stability or aesthetics. Non limiting examples of such counterions include halides (e.g., chlorine, fluorine, bromine, iodine), sulfate and methyl sulfate.

The cationic nitrogen-containing moiety of the cationic polymer is generally present as a substituent on all, or more typically on some, of the monomer units thereof. Thus, suitable cationic polymers for use in the anti-microbial compositions of the present invention include homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the *CTFA Cosmetic Ingredient Dictionary*, 3rd edition, edited by Estrin, Crosley, and Haynes, (The Cosmetic, Toiletry, and Fragrance Association, Inc., Washington, D.C. (1982)), which description is incorporated herein by reference.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers preferably have from $C_1$ to $C_7$ alkyl groups, more preferably from $C_1$ to $C_3$ alkyl groups. Other suitable spacer monomers include vinyl esters, vinyl alcohol (made by hydrolysis of polyvinyl acetate), maleic anhydride, propylene glycol, and ethylene glycol.

Suitable cationic protonated amino and quaternary ammonium monomers, for inclusion in the cationic polymers of the anti-microbial composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Suitable amine-substituted vinyl monomers for use herein include dialkyl-aminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydro-carbyls, more preferably $C_1$-$C_3$, alkyls.

Other suitable cationic polymers for use in the anti-microbial compositions herein include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A.) under the LUVIQUAT trade-name (e.g., LUVIQUAT FC 370); copolymers of 1-vinyl-2-pyrrolidone and dimethylaminoethyl methacrylate (referred to in the industry by CTFA as Polyquaternium-11) such as those commercially available from ISP Corporation (Wayne, N.J., U.S.A.) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from 3 to 5 carbon atoms, as described in U.S. Pat. No. 4,009,256, which description is incorporated herein by reference.

Other suitable cationic polymers for use in the anti-microbial composition include polysaccharide polymers, such as cationic cellulose derivatives and cationic starch derivatives. Suitable cationic polysaccharide polymers include those which conform to the formula

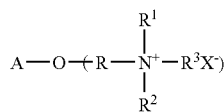

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are those polymers available from Amerchol Corp. (Edison, N.J., USA) in their Polymer JR and LR series of polymers, as salts of hydroxyethyl cellulose reacted with trimethyl ammonium substituted epoxide, referred to in the industry (CTFA) as Polyquaternium 10. Another type of preferred cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the trade name Polymer LM-200.

Other suitable cationic polymers include cationic guar gum derivatives, such as guar hydroxypropyltrimonium chloride, specific examples of which include the Jaguar series commercially available from Rhone-Poulenc Incorporated. Preferred cationic guar gum derivatives include Jaguar® C 13S and Jaguar® C 17 (both available from Rhodia Company). Other suitable cationic polymers include quaternary nitrogen-containing cellulose ethers, some examples of which are described in U.S. Pat. No. 3,962,418, which description is incorporated herein by reference herein. Other suitable cationic polymers include copolymers of etherified cellulose, guar and starch, some examples of which are described in U.S. Pat. No. 3,958,581, which description is incorporated herein by reference.

Other suitable cationic polymers for use in anti-microbial compositions of the present invention are copolymers of vinyl monomers, having cationic protonated amine or quaternary ammonium functionalities, reacted with water soluble monomers. Non-limiting examples of such monomers include: acrylamide, methacrylamide, alkyl and dialkyl acrylamides, alkyl and dialkyl methacrylamides, alkyl acrylate, alkyl methacrylate, vinyl caprolactone, vinyl pyrrolidone, and mixtures thereof. The alkyl and dialkyl substituted monomers preferably have from $C_1$ to $C_7$ alkyl groups, more preferably from $C_1$ to $C_3$ alkyl groups. Other suitable monomers include vinyl esters, vinyl alcohol (made by hydrolysis of polyvinyl acetate), maleic anhydride, propylene glycol, ethylene glycol, and mixtures thereof.

Suitable cationic protonated amino and quaternary ammonium monomers, for inclusion in the cationic polymers of the anti-microbial composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts; and vinyl quaternary ammonium monomers having cyclic cationic nitrogen-containing rings such as pyridinium, imidazolium, and quaternized pyrrolidones, such as alkyl vinyl imidazolium, alkyl vinyl pyridinium, and alkyl vinyl pyrrolidone salts. The alkyl portions of these monomers are preferably lower alkyls such as the $C_1$-$C_3$ alkyls.

Suitable amine-substituted vinyl monomers for use herein include, dialkylamino-alkyl acrylamide, and dialkylaminoalkyl methacrylamide, wherein the alkyl groups are preferably $C_1$ to $C_7$ hydrocarbyls, more preferably $C_1$ to $C_3$ alkyls.

Other suitable cationic polymers for use in the anti-microbial compositions of the present invention include: copolymers of 1-vinyl-2-pyrrolidone and 1-vinyl-3-methyl-imidazolium salt (e.g., chloride salt), known in the industry (CTFA) as Polyquaternium 16 (e.g. Luviquat® FC 370, available from BASF Wyandotte Corporation); copolymers of 1-vinyl-2-pyrrolidone and dimethylaminoethyl methacrylate, known in the industry (CTFA) as Polyquaternium 11 (e.g. Gafquat® 755N, available from ISP Corporation); cationic diallyl quaternary ammonium-containing polymers, including, for example, dimethyldiallylammonium chloride homopolymer, known in the industry (CTFA) as Polyquaternium 6; copolymers of acrylamide and dimethyldiallylammonium chloride, known in the industry (CTFA) as Polyquaternium 7; and mineral acid salts of amino-alkyl esters of homopolymers and copolymers of unsaturated $C_3$ to $C_5$ carboxylic acids, such as those described in U.S. Pat. No. 4,009,256, which description is incorporated herein by reference.

Still other cationic polymers for use in the anti-microbial compositions of the present invention are cationic modified proteins, such as lauryldimonium hydroxypropyl collagen (e.g. Croquat® L, available from Croda Corporation), or cocodimonium hydroxypropyl hydrolized hair keratin (e.g. Croquat® HH, available from Croda Corporation). Other cationic polymers include the polymeric quaternary salt prepared the reaction of adipic acid and dimethylaminopropylamine, reacted with dichloroethyl ether, known in the industry (CTFA) as Polyquaternium 2 (e.g. Mirapol® AD-1, available from Rhodia), and the polymeric quaternary salt prepared by the reaction of azelaic acid and dimethylaminopropylether, known in the industry (CTFA) as Polyquaternium 18 (e.g. Mirapolg AZ-1, available from Rhodia Corporation).

Yet other cationic polymers suitable for use herein are the Arquad® series of quaternary ammonium salts, available from Akzo Nobel. Other preferred cationic polymers for use herein include: Polymer KG30M (polyquaternium 10 and quaternized cellulose), Incroquat® behenyl trimonium methosulfate (cetearyl alcohol and behentrimonium methosulfate), available from Croda; Merquat® 5 (quaternary ammonium resin), available from Calgon; Gafquat® series 440 (cationic quaternized copolymers), available from ISP; Akypoquat® 131, available from Kao; Salcare® SC 60 (quaternary ammonium resin), or Salcare® SC95 or SC96 (cationic liquid dispersion thickeners), all available from Ciba; and Meadowquat® HG (PEG-2-dimeadowfoamamido-ethylmonium methosulfate), available from Fanning.

The cationic polymers herein may be either soluble in the anti-microbial composition, or preferably are soluble in a complex coacervate phase of the composition formed by a cationic polymer and an anionic detersive surfactant component described hereinbefore. Complex coacervates of the cationic polymer can also be formed with other charged materials in the anti-microbial composition.

Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries*, Vol. 106, April 1991, pp 49-54, C. J. van Oss, "Coacervation, Complex-Coacervation and Flocculation", *J. Dispersion Science and Technology*, Vol. 9 (5,6), 1988-89, pp 561-573, and D. J. Burgess, "Practical Analysis of Complex Coacervate Systems", *J. of Colloid and Interface Science*, Vol. 140, No. 1, November 1990, pp 227-238, which descriptions are incorporated herein by reference.

D. Styling Polymer

Certain embodiments of the anti-microbial compositions of the present invention may include a water-insoluble hair styling polymer. When present, concentrations of the styling polymer range from about 0.1% to about 10%, preferably from about 0.3% to about 7%, more preferably from about 0.5% to about 5%, by weight of the composition. These styling polymers are especially useful in styling shampoo embodiments of the present invention as they provide polymeric deposits on the hair after application from a shampoo composition. The polymer deposited on the hair has adhesive and cohesive strength and delivers styling primarily by forming welds between hair fibers upon drying, as is understood by those skilled in the art.

Many such polymers are known in the art, including water-insoluble organic polymers and water-insoluble silicone-grafted polymers, all of which are suitable for use in the anti-microbial compositions herein provided that they also have the requisite features or characteristics described hereinafter and are compatible with the essential components of the invention. Such polymers can be made by conventional or otherwise known polymerization techniques well known in the art, an example of which includes free radical polymerization.

Examples of suitable organic and silicone grafted polymers for use in the anti-microbial composition of the present invention are described in greater detail hereinafter.

1. Organic Styling Polymer

The hair styling polymers suitable for use in the anti-microbial composition of the present invention include organic hair styling polymers well known in the art. The organic styling polymers may be homopolymers, copolymers, terpolymers or other higher polymers, but must comprise one or more polymerizable hydrophobic monomers to thus render the resulting styling polymer hydrophobic and water-insoluble as defined herein. The styling polymers may therefore further comprise other water soluble, hydrophillic monomers provided that the resulting styling polymers have the requisite hydrophobicity and water insolubility.

As used herein, the term "hydrophobic monomer" refers to polymerizable organic monomers that can form with like monomers a water-insoluble homopolymer, and the term "hydrophilic monomer" refers to polymerizable organic monomers that can form with like monomers a water-soluble homopolymer.

The organic styling polymers preferably have a weight average molecular weight of at least about 20,000, preferably greater than about 25,000, more preferably greater than about 30,000, most preferably greater than about 35,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

The organic styling polymers also preferably have a glass transition temperature (Tg) or crystalline melting point (Tm) of at least about −20° C., preferably from about 20° C. to about 80° C., more preferably from about 20° C. to about 60° C. Styling polymers having these Tg or Tm values form styling films on hair that are not unduly sticky or tacky to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are within the ranges recited hereinabove.

The organic styling polymers are carbon chains derived from polymerization of hydrophobic monomers such as ethylenically unsaturated monomers, cellulosic chains or other carbohydrate-derived polymeric chains. The backbone may comprise ether groups, ester groups, amide groups, urethanes, combinations thereof, and the like.

The organic styling polymers may comprise one or more hydrophilic monomers in combination with the hydrophobic monomers described herein, provided that the resulting styling polymer has the requisite hydrophobic character and water-insolubility. Suitable hydrophilic monomers include, but are not limited to, acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), salts of any acids and amines listed above, and mixtures thereof. Preferred hydrophillic monomers include acrylic acid, N,N-dimethyl acrylamide, dimethylaminoethyl methacrylate, quaternized dimethyl aminoethyl methacrylate, vinyl pyrrolidone, salts of acids and amines listed above, and combinations thereof.

Suitable hydrophobic monomers for use in the organic styling polymer include, but are not limited to, acrylic or methacrylic acid esters of $C_1$-$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-methyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1 to about 18 carbon atoms, preferably from about 1 to about 12 carbon atoms; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred hydrophobic monomers include n-butyl methacrylate, isobutyl methacrylate, t-butyl acrylate, t-butyl methacrylate, 2-ethylhexyl methacrylate, methyl methacrylate, vinyl acetate, and mixtures thereof, more preferably t-butyl acrylate, t-butyl methacrylate, or combinations thereof.

When present, the styling polymers for use in the anti-microbial compositions preferably comprise from about 20% to 100%, more preferably from about 50% to about 100%, even more preferably from about 60% to about 100%, by weight of the hydrophobic monomers, and may further comprise from zero to about 80% by weight of hydrophilic monomers. The particular selection and combination of monomers for incorporation into the styling polymer will help determine its formulational properties. By appropriate selection and combination of, for example, hydrophilic and hydrophobic monomers, the styling polymer can be optimized for physical and chemical compatibility with the other components of the anti-microbial composition.

Examples of preferred organic styling polymers include t-butyl acrylate/2-ethylhexyl acrylate copolymers having a weight/weight ratio of monomers of about 95/5, about 90/10, about 80/20, about 70/30, about 60/40, and about 50/50; t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl acrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and about 50/50; vinyl pyrrolidone/vinyl acetate copolymers having a weight/weight ratio of monomers of about 10/90, and about 5/95; and mixtures thereof.

Especially preferred polymers are t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70/30, about 60/40, and about 50/50; and mixtures thereof.

Examples of other suitable styling polymers are described in U.S. Pat. No. 5,120,531, to Wells et al., issued Jun. 9, 1992; U.S. Pat. No. 5,120,532, to Wells et al., issued Jun. 9, 1992; U.S. Pat. No. 5,104,642, to Wells et al., issued Apr. 14, 1992; U.S. Pat. No. 4,272,511, to Papantoniou et al., issued Jun. 9, 1981; U.S. Pat. No. 5,672,576, to Behrens et al., issued Sep. 30, 1997; and U.S. Pat. No. 4,196,190, to Gehman et al., issued Apr. 1, 1980, which descriptions are incorporated herein by reference.

2. Silicone-Grafted Styling Polymer

Other suitable styling polymers for use in the anti-microbial composition of the present invention are silicone-grafted hair styling resins. These polymers may be used alone or in combination with the organic styling polymers described hereinbefore. Many such polymers suitable for use in the anti-microbial composition herein are known in the art. These polymers are characterized by polysiloxane moieties covalently bonded to and pendant from a polymeric carbon-based backbone.

The backbone of the silicone-grafted polymer is preferably a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups and the like. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The silicone-grafted styling polymers for use in the anti-microbial composition comprise "silicone-containing" (or "polysiloxane-containing") monomers, which form the silicone macromer pendant from the backbone, and non-silicone-containing monomers, which form the organic backbone of the polymer.

Preferred silicone-grafted polymers comprise an organic backbone, preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The polysiloxane macromer should have a weight average molecular weight of at least about 500, preferably from about 1,000 to about 100,000, more preferably from about 2,000 to about 50,000, most preferably about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Preferred silicone grafted polymers for use in the anti-microbial composition comprise monomer units derived from: at least one free radically polymerizable ethylenically unsaturated monomer or monomers and at least one free radically polymerizable polysiloxane-containing ethylenically unsaturated monomer or monomers.

The silicone grafted polymers suitable for use in the anti-microbial composition generally comprise from about 1% to about 50%, by weight, of polysiloxane-containing monomer units and from about 50% to about 99% by weight, of non-polysiloxane-containing monomers. The non-polysiloxane-containing monomer units can be derived from the hydrophilic and/or hydrophobic monomer units described hereinbefore.

The styling polymer for use in the anti-microbial composition can therefore comprise combinations of the hydrophobic and/or polysiloxane-containing monomer units described herein, with or without hydrophilic comonomers as described herein, provided that the resulting styling polymer has the requisite characteristics as described herein.

Suitable polymerizable polysiloxane-containing monomers include, but are not limited to, those monomers that conform to the formula:

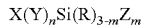

wherein X is an ethylenically unsaturated group copolymerizable with the hydrophobic monomers described herein, such as a vinyl group; Y is a divalent linking group; R is a hydrogen, hydroxyl, lower alkyl (e.g. $C_1$-$C_4$), aryl, alkaryl, alkoxy, or alkylamino; Z is a monovalent siloxane polymeric moiety having a number average molecular weight of at least about 500, which is essentially unreactive under copolymerization conditions, and is pendant from the vinyl polymeric backbone described above; n is 0 or 1; and m is an integer from 1 to 3. These polymerizable polysiloxane-containing monomers have a weight average molecular weight as described above.

A preferred polysiloxane-containing monomer conforms to the formula:

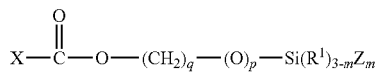

wherein m is 1, 2 or 3 (preferably m=1); p is 0 or 1; q is an integer from 2 to 6; $R^1$ is hydrogen, hydroxyl, lower alkyl, alkoxy, alkylamino, aryl, or alkaryl (preferably $R^1$ is alkyl); X conforms to the formula

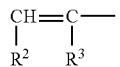

wherein $R^2$ is hydrogen or —COOH (preferably $R^2$ is hydrogen); $R^3$ is hydrogen, methyl or —CH$_2$COOH (preferably $R^3$ is methyl); Z conforms to the formula:

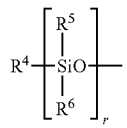

wherein $R^4$, $R^5$, and $R^6$ independently are lower alkyl, alkoxy, alkylamino, aryl, arylalkyl, hydrogen or hydroxyl (preferably $R^4$, $R^5$, and $R^6$ are alkyls); and r is an integer of about 5 or higher, preferably about 10 to about 1500 (most preferably r is from about 100 to about 250). Most preferably, $R^4$, $R^5$, and $R^6$ are methyl, p=0, and q=3.

Another preferred polysiloxane monomer conforms to either of the following formulas

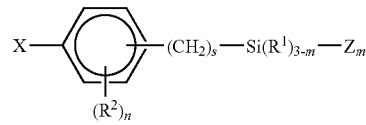

or

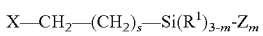

wherein: s is an integer from 0 to about 6, preferably 0, 1, or 2, more preferably 0 or 1; m is an integer from 1 to 3, preferably 1; $R^2$ is $C_1$-$C_{10}$ alkyl or $C_7$-$C_{10}$ alkylaryl, preferably C1-C6 alkyl or C7-C10 alkylaryl, more preferably C1-C2 alkyl; n is an integer from 0 to 4, preferably 0 or 1, more preferably 0.

The silicone grafted styling polymers suitable for use in the anti-microbial composition preferably comprise from about 50% to about 99%, more preferably from about 60% to about 98%, most preferably from about 75% to about 95%, by weight of the polymer, of non-silicone macromer-containing monomer units, e.g. the total hydrophobic and hydrophilic monomer units described herein, and from about 1% to about 50%, preferably from about 2% to about 40%, more preferably from about 5% to about 25%, of silicone macromer-containing monomer units, e.g. the polysiloxane-containing monomer units described herein. The level of hydrophilic monomer units can be from about 0% to about 70%, preferably from about 0% to about 50%, more preferably from about 0% to about 30%, most preferably from about 0% to about 15%; the level of hydrophobic monomer units, can be from 30% to about 99%, preferably from about 50% to about 98%, more preferably from about 70% to about 95%, most preferably from about 85% to about 95%.

Examples of some suitable silicone grafted polymers for use in the anti-microbial composition herein are listed below. Each listed polymer is followed by its monomer composition as weight part of monomer used in the synthesis:

(i) t-butylacrylatye/t-butyl-methacrylate/2-ethylhexyl-methacrylate/PDMS macromer-20,000 molecular weight macromer 31/27/32/10

(ii) t-butylmethacrylate/2-ethylhexyl-methacrylate/PDMS macromer-15,000 molecular weight macromer 75/10/15

(iii) t-butylmethacrylate/2-ethylhexyl-acrylate/PDMS macromer-10,000 molecular weight macromer 65/15/20

(iv) t-butylacrylate/2-ethylhexyl-acrylate/PDMS macromer-14,000 molecular weight macromer 77/11/12

(v) t-butylacrylate/2-ethylhexyl-methacrylate/PDMS macromer-13,000 molecular weight macromer 81/9/10

Examples of other suitable silicone grafted polymers for use in the anti-microbial composition of the present invention are described in EPO Application 90307528.1, published as EPO Application 0 408 311 A2 on Jan. 11, 1991, Hayama, et al.; U.S. Pat. No. 5,061,481, issued Oct. 29, 1991, Suzuki et al.; U.S. Pat. No. 5,106,609, Bolich et al., issued Apr. 21, 1992; U.S. Pat. No. 5,100,658, Bolich et al., issued Mar. 31, 1992; U.S. Pat. No. 5,100,657, Ansher-Jackson, et al., issued Mar. 31, 1992; U.S. Pat. No. 5,104,646, Bolich et al., issued Apr. 14, 1992; U.S. Ser. No. 07/758,319, Bolich et al, filed Aug. 27, 1991, U.S. Ser. No. 07/758,320, Torgerson et al., filed Aug. 27, 1991, which descriptions are incorporated herein by reference.

E. Cationic Spreading Agent

The anti-microbial compositions of the present invention may further comprise select cationic materials which act as spreading agents. The spreading agents for use in the composition are select quaternary ammonium or protonated amino compounds defined in greater detail hereinafter. These select spreading agents are useful to enhance the morphology of the styling polymer deposit on the hair so that more efficient adhesion between hair fibers results in improved styling performance. The concentration of the select spreading agents in the composition range from about 0.05% to about 5%, preferably from about 0.1% to about 2%, more preferably from about 0.5% to about 1.5%, by weight of the anti-microbial composition.

The select spreading agents are quaternary ammonium or amino compounds having 2, 3 or 4 N-radicals which are substituted or unsubstituted hydrocarbon chains having from about 12 to about 30 carbon atoms, wherein the substituents includes nonionic hydrophilic moieties selected from alkoxy, polyoxalkylene, alkylamido, hydroxyalkyl, alkylester moieties, and mixtures thereof. Suitable hydrophile-containing radicals include, for example, compounds having nonionic hydrophile moieties selected from the group consisting of ethoxy, propoxy, polyoxyethylene, polyoxypropylene, ethylamido, propylamido, hydroxymethyl, hydroxyethyl, hydroxypropyl, methylester, ethylester, propylester, or mixtures thereof. The select spreading agents are cationic and must be positively charged at the pH of the shampoo compositions. Generally, the pH of the shampoo composition will be less than about 10, typically from about 3 to about 9, preferably from about 4 to about 8.

Select cationic spreading agents for use in the composition include those corresponding to the formula:

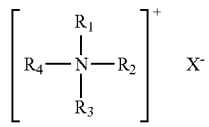

wherein $R_1$, and $R_2$ are independently a saturated or unsaturated, substituted or unsubstituted, linear or branched hydrocarbon chain having from about 12 to about 30 carbon atoms, preferably from about 18 to about 22 carbon atoms, and wherein the hydrocarbon chain can contain one or more hydophilic moieties selected from the alkoxy, polyoxyalkylene, alkylamido, hydroxyalkyl, alkylester, and mixtures thereof; $R_3$ and $R_4$ are independently a hydrogen, or a saturated or unsaturated, substituted or unsubstituted, linear or branched hydrocarbon chain having from about 1 to about 30 carbon atoms, or a hydrocarbon having from about 1 to about 30 carbon atoms containing one or more aromatic, ester, ether, amido, amino moieties present as substituents or as linkages in the chain, and wherein the hydrocarbon chain can contain one or more hydophilic moieties selected from the alkoxy, polyoxyalkylene, alkylamido, hydroxyalkyl, alkylester, and mixtures thereof; and X is a soluble salt forming anion preferably selected from halogen (especially chlorine), acetate, phosphate, nitrate, sulfonate, and alkylsulfate radicals.

An example of a select spreading agent for use in the composition include those corresponding to the formula:

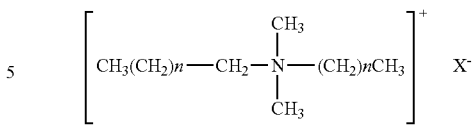

wherein n is from 10-28, preferably 16, and X is a water soluble salt forming anion (e.g., Cl, sulfate, etc.).

Other examples of select cationic spreading agents for use in the composition include those corresponding to the formula:

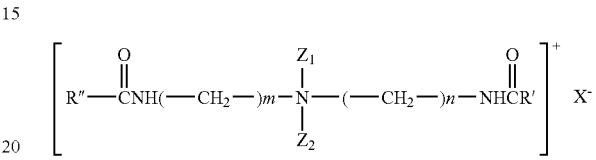

wherein $Z_1$ and $Z_2$ are independently saturated or unsaturated, substituted or unsubstituted, linear or branched hydrocarbons, and preferably $Z_1$ is an alkyl, more preferably methyl, and $Z_2$ is a short chain hydroxyalkyl, preferably hydroxymethyl or hydroxyethyl; n and m are independently integers from 1 to 4, inclusive, preferably from 2 to 3, inclusive, more preferably 2; R' and R" are independently substituted or unsubstituted hydrocarbons, preferably $C_{12}$-$C_{20}$ alkyl or alkenyl; and X is a soluble salt forming anion (e.g., Cl, sulfate, etc.).

Nonlimiting examples of suitable cationic spreading agents include ditallowdimethyl ammonium chloride, ditallowdimethyl ammonium methyl sulfate, dihexadecyl dimethyl ammonium chloride, di-(hydrogenated tallow) dimethyl ammonium chloride, dioctadecyl dimethyl ammonium chloride, dieicosyl dimethyl ammonium chloride, didocosyl dimethyl ammonium chloride, di-(hydrogenated tallow) dimethyl ammonium acetate, dihexadecyl dimethyl ammonium acetate, ditallow dipropyl ammonium phosphate, ditallow dimethyl ammonium nitrate, di-(coconutalkyl) dimethyl ammonium chloride, ditallowamidoethyl hydroxypropylmonium methosulfate (commercially available as Varisoft 238), dihydrogenated tallowamidoethyl hydroxyethylmonium methosulfate (commercially available as Varisoft 110), ditallowamidoethyl hydroxyethylmonium methosulfate (commercially available as Varisoft 222), and di(partially hardened soyoylethyl) hydroxyethylmonium methosulfate (commercially available as Armocare EQ-S). Ditallowdimethyl ammonium chloride, ditallowamidoethyl hydroxypropylmonium methosulfate, dihydrogenated tallowamidoethyl hydroxyethylmonium methosulfate, ditallowamidoethyl hydroxyethylmonium methosulfate, and di(partially hardened soyoylethyl) hydroxyethylmonium methosulfate are particularly preferred quaternary ammonium cationic surfactants useful herein.

Other suitable quaternary ammonium cationic surfactants are described in M.C. Publishing Co., *McCutcheion's Detergents & Emulsifiers*, (North American edition 1979); Schwartz, et al., *Surface Active Agents. Their Chemistry and Technology*, New York: Interscience Publishers, 1949; U.S. Pat. No. 3,155,591, to Hilfer, issued Nov. 3, 1964; U.S. Pat. No. 3,929,678 to Laughlin et al., issued Dec. 30, 1975; U.S. Pat. No. 3,959,461 to Bailey et al, issued May 25, 1976; and U.S. Pat. No. 4,387,090 to Bolich Jr., issued Jun. 7, 1983, which descriptions are incorporated herein by reference.

F. Silicone Conditioning Agent

The anti-microbial compositions of the present invention may, in some embodiments, include a silicone conditioning agent at concentrations effective to provide skin and/or hair conditioning benefits. When present, such concentrations range from about 0.01% to about 10%, preferably from about 0.1% to about 8%, more preferably from about 0.1% to about 5%, most preferably from about 0.2% to about 3%, by weight of the anti-microbial compositions.

The optional silicone conditioning agents are insoluble in the anti-microbial compositions, and are preferably nonvolatile. Such silicone conditioning agents are preferably used in shampoo embodiments of the present invention. Typically the silicone conditioning agent will be intermixed in the composition so as to be in the form of a separate, discontinuous phase of dispersed, insoluble particles, also referred to as droplets. The optional silicone conditioning agent phase may comprise a silicone fluid conditioning agent such as a silicone fluid and can also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference.

The optional silicone conditioning agent phase may comprise volatile silicone, nonvolatile silicone, or combinations thereof. Typically, if volatile silicones are present, it will be incidental to their use as a solvent or carrier for commercially available forms of nonvolatile silicone materials ingredients, such as silicone gums and resins.

The optional silicone hair conditioning agents for use in the anti-microbial compositions preferably have a viscosity of from about 20 to about 2,000,000 centistokes, more preferably from about 1,000 to about 1,800,000 centistokes, even more preferably from about 50,000 to about 1,500,000 centistokes, as measured at 25° C.

Background material on silicones including sections discussing silicone fluids, gums, and resins, as well as manufacture of silicones, can be found in Encyclopedia of Polymer Science and Engineering, Volume 15, Second Edition, pp 204-308, John Wiley & Sons, Inc., 1989, incorporated herein by reference.

Optional silicone fluids include silicone oils which are flowable silicone materials having a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and combinations thereof. Other insoluble, nonvolatile silicone fluids having hair conditioning properties can also be used.

Optional silicone oils include polyalkyl or polyaryl siloxanes which conform to the following formula (I)

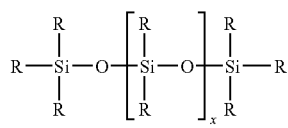

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkylamine, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the anti-microbial compositions, are chemically stable under normal use and storage conditions, are insoluble in the anti-microbial compositions herein, and are capable of being deposited on and conditioning the hair.

The two R groups on the silicon atom of each monomeric silicone unit may represent the same or different groups. Preferably, the two R groups represent the same group.

Preferred alkyl and alkenyl substituents are $C_1$-$C_5$ alkyls and alkenyls, more preferably from $C_1$-$C_4$, most preferably from $C_1$-$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$-$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition hereof.

Suitable alkylamino substituted silicones include those which conform to the following structure (II)

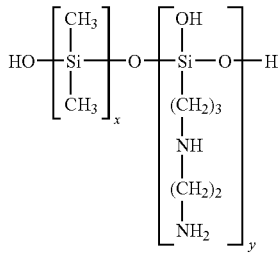

wherein x and y are integers. This polymer is also known as "amodimethicone".

Suitable cationic silicone fluids include those which conform to the formula (III) $(R_1)_a G_{3-a}$—Si—(—$OSiG_2)_n$-(—$OSiG_b(R_1)_{2-b})_m$—O—$SiG_{3-a}(R_1)_a$, wherein G is selected from the group consisting of hydrogen, phenyl, hydroxy, $C_1$-$C_8$ alkyl and preferably methyl; a is 0 or an integer having a value from 1 to 3, preferably 0; b is 0 or 1, preferably 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical conforming to the formula $CqH_{2q}L$ in which q is an integer having a value of from 2 to 8 and L is selected from the following groups:

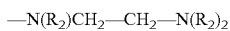

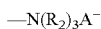

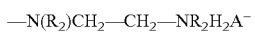

in which $R_2$ is selected from the group consisting of hydrogen, phenyl, benzyl, a saturated hydrocarbon radical, preferably an alkyl radical containing from 1 to 20 carbon atoms, and $A^-$ is a halide ion.

An especially preferred cationic silicone corresponding to formula (III) is the polymer known as "trimethylsilylamodimethicone", of formula (IV):

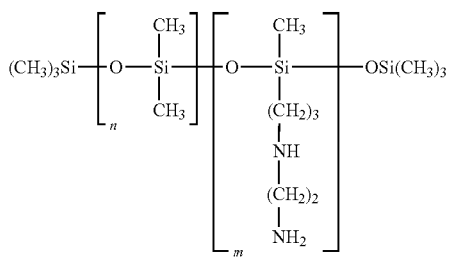

Other silicone cationic polymers which can be used in the anti-microbial compositions are represented by the formula (V):

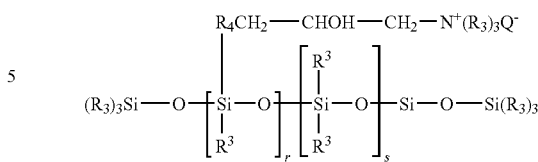

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$-$C_{18}$ alkylene radical or a $C_1$-$C_{18}$, and more preferably $C_1$-$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

Other optional silicone fluids are the insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, Chemistry and Technology of Silicones, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

Another category of nonvolatile, insoluble silicone fluid conditioning agents are the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (I) above, as well as cyclic polysiloxanes such as those represented by Formula (VI) below:

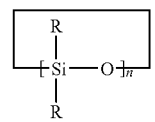

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$-$C_5$ alkyl or alkenyl substituents, e.g., allylphenyl, methyl phenyl and ethyl phenyl, vinyl phenyls such as styrenyl, and phenyl alkynes (e.g. phenyl $C_2$-$C_4$ alkynes). Heterocyclic aryl groups include substituents derived from furan, imidazole, pyrrole, pyridine, etc. Fused aryl ring substituents include, for example, napthalene, coumarin, and purine.

In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm$^2$, typically at least about 27 dynes/cm$^2$. Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$-$C_4$ alkyl (most preferably methyl), hydroxy, $C_1$-$C_4$ alkylamino (especially —$R^1NHR^2NH2$ where each $R^1$ and $R^2$ independently is a $C_1$-$C_3$ alkyl, alkenyl, and/or alkoxy. High refractive index polysiloxanes are available from Dow Corning Corporation (Midland, Mich., U.S.A.) Huls America (Piscataway, N.J., U.S.A.), and General Electric Silicones (Waterford, N.Y., U.S.A.).

When high refractive index silicones are used in anti-dandruff and conditioning shampoo embodiments of the anti-microbial compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions. Generally, an amount of the spreading agent is used that is sufficient to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture may improve shine of the hair References disclosing examples of some suitable silicone fluids for use in shampoo compositions include U.S. Pat. No. 2,826,551, U.S. Pat. No. 3,964,500, U.S. Pat. No. 4,364,837, British Patent 849,433, and Silicon Compounds, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

G. Organic Conditioning Oils

The anti-microbial compositions of the present invention, in some embodiments, may include from about 0.05% to about 3%, by weight of the composition, preferably from about 0.08% to about 1.5%, more preferably from about 0.1% to about 1%, of at least one organic conditioning oil as the conditioning agent, either alone, or in combination with other conditioning agents, such as the silicones described above.

Such conditioning oils may add shine and luster to the hair, enhance dry combing of hair and/or enhance dry skin or hair feel.

The organic conditioning oils suitable for use as the conditioning agent herein are preferably low viscosity, water insoluble, liquids selected from the hydrocarbon oils, polyolefins, fatty esters, and mixtures thereof. The viscosity, as measured at 40° C., of such organic conditioning oils is preferably from about 1 centipoise to about 200 centipoise, more preferably from about 1 centipoise to about 100 centipoise, most preferably from about 2 centipoise to about 50 centipoise.

1. Hydrocarbon Oils

Suitable organic conditioning oils for use as conditioning agents in the anti-microbial compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

2. Polyolefins

Organic conditioning oils for use in the anti-microbial compositions of the present invention can also include liquid polyolefins, more preferably liquid poly-α-olefins, most preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

3. Fatty Esters

Other suitable organic conditioning oils for use as the conditioning agent in the anti-microbial compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Suitable for use in the anti-microbial compositions of the present invention are alkyl and alkenyl esters of fatty acids having from about $C_{10}$ to about $C_{22}$ aliphatic chains, and alkyl and alkenyl fatty alcohol carboxylic acid esters having a $C_{10}$ to about $C_{22}$ alkyl and/or alkenyl alcohol-derived aliphatic chain, and mixtures thereof. Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the anti-microbial compositions of the present invention are mono-carboxylic acid esters of the general formula R'COOR, wherein R' and R are alkyl or alkenyl radicals, and the sum of carbon atoms in R' and R is at least 10, preferably at least 20. The mono-carboxylic acid ester need not necessarily contain at least one chain with at least 10 carbon atoms; rather the total number of aliphatic chain carbon atoms must be least 10. Specific non-limiting examples of mono-carboxylic acid esters include: isopropyl myristate, glycol stearate, and isopropyl laurate.

Still other fatty esters suitable for use in the anti-microbial compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, adipic acid, hexanoic acid, heptanoic acid, and octanoic acid). Specific non-limiting examples of di- and tri-alkyl and alkenyl esters of carboxylic acids include isocetyl stearoyl stearate, diisopropyl adipate, and tristearyl citrate.

Other fatty esters suitable for use in the anti-microbial compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the anti-microbial compositions of the present invention are glycerides, including, but not limited to, mono-, di-, and tri-glycerides, preferably di- and tri-glycerides, most preferably triglycerides. For use in the anti-microbial compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the anti-microbial compositions of the present invention are water insoluble synthetic fatty esters. Some preferred synthetic esters conform to the general Formula (IX):

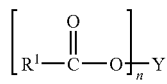

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

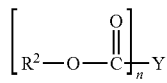

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

It is believed that the inclusion of synthetic esters can provide improved wet hair feel, such as in shampoo embodiments, particularly when used in combination with a cationic polymer (described below). These synthetic esters improve wet hair feel by reducing the slimy or excessively conditioned feel of wet hair that has been conditioned by a cationic polymer.

Commercially available synthetic fatty esters for use in the anti-microbial compositions of the present invention include: "P-43" ($C_8$-$C_{10}$ triester of trimethylolpropane), "MCP-684" (tetraester of 3,3 diethanol-1,5 pentadiol), MCP 121' ($C_8$-$C_{10}$ diester of adipic acid), all of which are available from Mobil Chemical Company.

H. Other Conditioning Agents

Also suitable for use in the compositions herein are the conditioning agents described by the Procter & Gamble Company in U.S. Pat. Nos. 5,674,478, and 5,750,122, both of which are incorporated herein in their entirety by reference. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal), all of which descriptions are incorporated herein by reference.

Some other preferred silicone conditioning agents for use in the compositions of the present invention include: "ABIL® S 201" (dimethicone/sodium PG-propyldimethicone thiosulfate copolymer), available from Goldschmidt; "DC Q2-8220" (trimethylsilyl amodimethicone) available from Dow Corning; "DC 949" (amodimethicone, cetrimonium chloride, and Trideceth-12), available from Dow Corning; "DC 749" (cyclomethicone and trimethylsiloxysilicate), available from Dow Corning; "DC2502" (cetyl dimethicone), available from Dow Corning; "BC97/004" and "BC 99/088" (amino functionalized silicone microemulsions), available from Basildon Chemicals; "GE SME253" and "SM2115-D2" and "SM2658" and "SF1708" (amino functionalized silicone microemulsions), available from General Electric; siliconized meadowfoam seed oil, available from Croda; and those silicone conditioning agents described by GAF Corp. in U.S. Pat. No. 4,834,767 (quaternized amino lactam), by Biosil Technologies in U.S. Pat. No. 5,854,319 (reactive silicone emulsions containing amino acids), and by Dow Corning in U.S. Pat. No. 4,898,585 (polysiloxanes), all of which descriptions are incorporated herein by reference.

I. Polyalkylene Glycol

The anti-microbial compositions of the present invention may, in some embodiments, especially hair styling shampoo embodiments, further comprise selected polyalkylene glycols in amounts effective to enhance the conditioned feel of the hair, to mitigate the coated hair feel resulting from addition of a cationic deposition polymer, and to enhance the styling performance of a hair styling shampoo. Effective concentrations of the selected polyethylene glycols range from about 0.025% to about 1.5%, preferably from about 0.05% to about 1.0%, more preferably from about 0.1% to about 0.5%, by weight of the shampoo composition.

The polyalkylene glycols suitable for use in the anti-microbial compositions are characterized by the general formula:

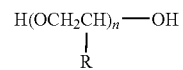

wherein R is hydrogen, methyl or mixtures thereof, preferably hydrogen, and n is an integer having an average value of from about 1,500 to about 25,000, preferably from about 2,500 to about 20,000, and more preferably from about 3,500 to about 15,000. When R is hydrogen, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist.

Specific examples of suitable polyethylene glycol polymers include "PEG-14 M" wherein R is hydrogen and n has an average value of about 14,000 ("PEG-14 M" is also known as "POLYOX WSR® N-3000" available from Union Carbide) and "PEG-23 M" wherein R is hydrogen and n has an average value of about 23,000 ("PEG-23 M" is also known as "POLYOX WSR® N-12K" available from Union Carbide).

Suitable polyalkylene polymers include polypropylene glycols and mixed polyethylene/polypropylene glycols.

J. Other Optional Ingredients

The anti-microbial compositions of the present invention may, in some embodiments, further comprise additional optional components known or otherwise effective for use in hair care or personal care products. The concentration of such optional ingredients generally ranges from zero to about 25%, more typically from about 0.05% to about 25%, even more typically from about 0.1% to about 15%, by weight of the composition. Such optional components should also be physically and chemically compatible with the essential components described herein, and should not otherwise unduly impair product stability, aesthetics or performance.

Non-limiting examples of optional components for use in the anti-microbial composition include anti-static agents, foam boosters, anti-dandruff agents in addition to the anti-dandruff agents described above, viscosity adjusting agents and thickeners, pH adjusting agents (e.g. sodium citrate, citric acid, succinic acid, phosphoric acid, sodium hydroxide, and sodium carbonate), preservatives (e.g. DMDM hydantoin), anti-microbial agents (e.g. triclosan or triclocarbon), dyes, organic solvents or diluents, pearlescent aids, perfumes, fatty alcohols, proteins, skin active agents, sunscreens, vitamins (such as retinoids including retinyl propionate, vitamin E such as tocopherol acetate, panthenol, and vitamin B3 compounds including niacinamide), emulsifiers, and pediculocides.

Optional anti-static agents such as water-insoluble cationic surfactants may be used, typically in concentrations ranging from about 0.1% to about 5%, by weight of the composition. Such anti-static agents should not unduly interfere with the in-use performance and end-benefits of the anti-microbial composition; particularly, the anti-static agent should not interfere with the anionic surfactant. A specific non-limiting example of a suitable anti-static agents is tricetyl methyl ammonium chloride.

Optional foam boosters for use in the anti-microbial compositions described herein include fatty ester (e.g. $C_8$-$C_{22}$) mono- and di ($C_1$-$C_5$, especially $C_1$-$C_3$) alkanol amides. Specific non-limiting examples of such foam boosters include coconut monoethanolamide, coconut diethanolamide, and mixtures thereof.

Optional viscosity modifiers and thickeners may used, typically in amounts effective for the anti-microbial compositions of the present invention to generally have an overall viscosity from about 1,000 csk to about 20,000 csk, preferably from about 3,000 csk to about 10,000 csk. Specific non-limiting examples of such viscosity modifiers and thickeners include: sodium chloride, sodium sulfate, and mixtures thereof.

Methods of Manufacture

The anti-microbial compositions of the present invention may be prepared by any known or otherwise effective technique, suitable for providing an anti-microbial composition provided that the resulting composition provides the excellent anti-microbial benefits described herein. Methods for preparing the anti-dandruff and conditioning shampoo embodiments of the present invention include conventional formulation and mixing techniques. A method such as that described in U.S. Pat. No. 5,837,661, which description is incorporated herein by reference, could be employed, wherein the anti-microbial agent of the present invention would typically be added in the same step as the silicone premix is added in the '661 description.

Methods of Use

The topical anti-microbial compositions of the present invention may be used in direct application to the skin or in a conventional manner for cleansing skin and hair and controlling microbial infection (including fungal, viral, or bacterial infections) on the skin or scalp. Directly applied compositions, such as powders, are used by applying an effective amount of the composition, typically from about 1 g to about 20 g, to the skin, for example the feet. The cleansing compositions herein are useful for cleansing the hair and scalp, and other areas of the body such as underarm, feet, and groin areas and for any other area of skin in need of treatment. An effective amount of the composition, typically from about 1 g to about 50 g, preferably from about 1 g to about 20 g of the composition, for cleansing hair, skin or other area of the body, is topically applied to the hair, skin or other area that has preferably been wetted, generally with water, and then rinsed off. Application to the hair typically includes working the shampoo composition through the hair.

A preferred method for providing anti-microbial (especially anti-dandruff) efficacy with a shampoo embodiment comprises the steps of: (a) wetting the hair with water, (b) applying an effective amount of the anti-microbial shampoo composition to the hair, and (c) rinsing the anti-microbial shampoo composition from the hair using water. These steps may be repeated as many times as desired to achieve the cleansing, conditioning, and anti-microbial/anti-dandruff benefits sought.

It is also contemplated that when the anti-microbial active employed is zinc pyrithione, and/or if other optional hair growth regulating agents are employed, the anti-microbial compositions of the present invention, may, provide for the regulation of growth of the hair. The method of regularly using such shampoo compositions comprises repeating steps a, b, and c (above).

It is also contemplated that the compositions herein may be employed as leave-on compositions. This method for providing anti-microbial efficacy to the skin or hair comprises the steps of (A) applying an effective amount of the shampoo composition to the skin or hair, and (B) leaving the product on the hair for a sufficient amount of time to allow for efficacy. The remaining product may then be later rinsed from the hair with water or brushed out of the hair with any common implement or the hands.

EXAMPLES

The composition of the invention can be made by mixing one or more selected metal ion sources and one or more metal salts of pyrithione in an appropriate media or carrier, or by adding the individual components separately to the skin or hair cleansing compositions. Useful carriers are discussed more fully above.

The following examples are intended to illustrate, but in no way limit the scope of the present invention. All parts and percentages are by weight and all temperatures are in degrees Celsius unless explicitly stated otherwise.

Example 1

The Effect of Combining ZPT with Metal Ions on the Minimum Inhibitory Concentration (MIC) of Metal Ions Experiments were conducted to investigate the efficacy of the composition of the present invention to inhibit the survival, growth, and proliferation of microorganisms in topical compositions. The test microorganism was *Malassezia furfur*. The testing principle employed, Minimum Inhibitory Concentration (MIC), is discussed below, and the results are tabulated in Table 1.

The Minimum Inhibitory Concentration is indicative of anti-fungal efficacy. Generally, the lower the value of the composition, the better its anti-fungal efficacy, due to increased inherent ability of the anti-dandruff agent to inhibit the growth of microorganisms.

*Malassezia furfur* was grown in a flask containing mDixon medium (see E. Gueho, et al. Antoinie Leeuwenhoek (1996), no. 69, 337-55, which description is incorporated by reference herein). Dilutions of solubilized anti-microbial active were then added to test tubes containing molten mDixon agar. *M. furfur* inoculum was added to each tube of molten agar, the tube vortexed, and the contents poured into separate sterile petri dishes. After the plates are incubated, they were observed for visible *M. furfur* growth. The lowest tested dilution of anti-microbial active that yields no growth is defined as the Minimal Inhibitory Concentration (MIC).

Equipment/Reagents

| | |
|---|---|
| Microbe | *Malassezia furfur* (ATCC 14521) |
| Erlenmeyer flask | 250 ml |
| Agar medium | 9.5 ml mDixon agar per concentration per active tested |
| Solvent | water, dimethyl sulfonyl oxide ("DMSO") |
| Zinc pyridinethione | ZPT having an average particle size of about 2.5 μm, preserved in "DARVAN ™," available from Arch |
| Test tubes | 2 tubes per anti-microbial active per concentration per active tested, sterilized, size = 18 mm × 150 mm |
| Petri dishes | 2 dishes per anti-microbial active per concentration per active tested, sterilized, size = 15 mm × 100 mm |

Experimental Procedure

1) *Malassezia furfur* was grown in a 250 ml Erlenmeyer flask containing 100 ml "mDIXON" medium at 320 rpm and 30° C. until turbid.
2) Selected dilutions were prepared using an appropriate dilution series, of the anti-microbial active or combination in solvent, which allowed the sample active to be solubilized prior to addition to the final test agar. For each concentration of the ZPT samples, the solvent was "DMSO"; for other samples, the solvent was water or "DMSO" or other suitable solvent.
3) 0.25 ml dilutions of anti-microbial active were added to test tubes containing 9.5 ml molten "mDIXON" agar (held at 45° C. in a water bath).
4) 0.25 *M. furfur* inoculum (adjusted to $5 \times 10^5$ cfu/ml by direct count) was added to each test tube of molten agar.
5) Each tube was vortexed, and the contents poured into separate petri dishes.
6) After the agar solidified, the plates inverted and incubated at 30° for 5 days.
7) The plates were then observed for visible *M. furfur* growth.

Table 1 shows the results of experiments testing the efficacy of ZPT in combination with several different metal ion sources against the *M. furfur* microorganism.

As shown in Table 1, it required at least 50 ppm of metal ions alone to inhibit fungal growth. When using ZPT alone, it requires 8 ppm to inhibit fungal growth. Sub-MIC levels of ZPT were tested in combination with various metals to determine the resulting MIC of the metal ion. As clearly indicated in Table 1, the addition of metal ions served to potentiate the ZPT, thereby achieving MIC with sub-MIC levels of ZPT. For instance, it is shown that a combination of 4 ppm ZPT with less than 0.005 ppm of copper ions achieved the MIC. However, neither 4 ppm of ZPT or 0.005 ppm of copper ion would achieve the MIC level alone.

Minimum Inhibitory Concentration (MIC) Data

TABLE 1

Data for $Cu^{2+}$, $Zn^{2+}$, $Ni^{2+}$, $Hg^{2+}$ Alone and in Combination with ZPT

| | MIC (ppm of metal ion) | | | |
|---|---|---|---|---|
| | Alone | +4 ppm ZPT* | +2 ppm ZPT* | +0.5 ppm ZPT* |
| Copper (2+) | 5000 | <0.005 | <0.5 | 5000 |
| Zinc (2+) | 5000 | 5 | 50 | 500 |
| Nickel (2+) | 500 | 50 | | |
| Mercury (2+) | 50 | 5 | | |

*$MIC_{ZPT}$ = 8 ppm

Example 2

The Effect of Metal Ions on the Kill Rate Results of Zinc Pyrithione

Experiments were conducted to investigate the efficacy of the composition of the present invention to inhibit the survival, growth, and proliferation of microorganisms in topical compositions. The test microorganism was *Malassezia furfur*. The testing principle employed, Kill Rate Test (KRT), is discussed below, and the results are tabulated in Tables 2(a) and 2(b).

The Kill Rate Test (KRT) results are indicative of anti-fungal efficacy. Generally, the greater the inhibition of fungal growth in this test, the better the anti-fungal efficacy of the compound(s) tested.

A flask containing mDixon broth medium (see Gueho, et al. Antoinie Leeuwenhoek (1996), no. 69, 337-55, which description is incorporated by reference herein) was inoculated with *Malassezia furfur*. Specific concentrations of active(s) were then added to the flask. Samples were then withdrawn from the flask at specified time points, diluted in sterile water, and spread across the surface of a mDixon agar plate. After the plates were incubated, they were observed for visible *M. furfur* growth by counting the number of colonies present and converting this number into colony forming units (CFU)/ml mDixon broth.

The lower the CFU/ml count, the better activity the active(s) have against *M. furfur*.

Equipment/Reagents

| | |
|---|---|
| Microbe | *Malassezia furfur* (ATCC 14521) |
| Erlenmeyer flask | 125 ml, sterilized, capped, 2 for growing *M. furfur* inoculum; 1 for each active combination per concentration |
| Solvent | water, dimethyl sulfonyl oxide ("DMSO"), |
| Broth medium | 41 g mDixon broth per active combination per concentration; 42 g mDixon broth per negative control |
| Agar medium | 10-15 ml mDixon broth per plate poured; 18 plates per active combination per concentration |
| Zinc pyridinethione | ZPT having an average particle size of about 2.5 mm, available from Arch |
| Petri dishes | 18 plates per active combination per concentration, sterilized, size = 15 mm × 100 mm |

Experimental Procedure

1. *M. furfur* (ATCC 14521) cultures were brought to log phase overnight in 2 Erlenmeyer flasks (125 ml) each containing 75 ml mDixon broth.
2. 41.0 g mDixon broth was prepared in a 125 ml Erlenmeyer flask containing 0.05% or 0.5% of the metal ion to be tested in combination with ZPT.

3. 20 g of a 500 ppm ZPT solution was prepared in DMSO by adding 0.010 mg ZPT to 19.990 g DMSO.
4. 1.0 g of the 500 ppm ZPT solution was added to the 41 g of broth/active from step 2 above giving 42 g in each flask.
5. 42 g mDixon broth was prepared in a 125 ml Erlenmeyer flask (for the negative control)
6. 41 g mDixon broth+1 g ZPT solution was prepared in a 125 ml Erlenmeyer flask (for the ZPT control)
7. From the log phase culture, 8.0 g *M. furfur* inoculum was added to each flask, bringing the weight of the broth/inoculum/actives to 50.0 g.
8. 0 hour time point samplings were performed according to the following methodology:
   a) Withdraw 1.1 ml broth from flasks.
   b) Spread 0.1 ml across surface of mDixon agar plate.
   c) Perform 10-1, 10-2, 10-3, 10-4 and 10-5 dilutions of the sample and spread 0.1 ml of these across separate mDixon agar plates. (For the 0 and 4 hour time points, only plate out 10-3, 10-4 and 10-5 dilutions)
   d) Invert and incubate plates 5-7 days at 30C.
   e) Determine viability by counting colonies and converting to CFU/ml.
9. For $Mg^{2+}$, $Ag^+$, $Mn^{2+}$, $Bi^{3+}$, and $Na^+$ Step 8 was repeated at the 24 and 48 hour time points. For $Zn^{2+}$ and $Cu^{2+}$, Step 8 was repeated at the 4, 24, and 48 hour time points.

Tables 2(a) and 2(b) show the results of experiments testing the efficacy of metal ion sources in combination with ZPT against the *M. furfur* microorganism.

As basis for comparison in Tables 2(a) and 2(b), the test results for the tested materials should be lower than the negative control at each particular data point in order to show quick efficacy. The closer to zero the resulting data point is, the quicker the efficacy of the material tested. Therefore, it is clear from the data presented that, for instance, 0.05% of copper sulfate in combination with 10 ppm ZPT works faster and is therefore more efficacious, than either 0.05% of copper sulfate or ZPT alone. The KRT data presented below therefore clearly indicate the potentiation of ZPT by the metal ion source.

TABLE 2(a)

Data for $Mg^{2+}$, $Ag^+$, $Mn^{2+}$, $Bi^{3+}$, $Na^+$

| | Plate Area Colonized (mm2) | | |
| --- | --- | --- | --- |
| | 0 Hours | 24 Hours | 48 Hours |
| Negative Control | 3.97E+06 | 1.44E+07 | 5.80E+06 |
| 10 ppm ZPT | 3.97E+06 | 2.52E+05 | 2.30E+03 |
| 0.05% MgSO$_4$ | 3.97E+06 | 4.35E+06 | 9.68E+06 |
| 0.05% MgSO$_4$ + 10 ppm ZPT | 3.97E+06 | 9.90E+04 | 1.41E+03 |
| 0.5% MgSO$_4$ | 3.97E+06 | 1.81E+07 | 9.50E+06 |
| 0.5% MgSO$_4$ + 10 ppm ZPT | 3.97E+06 | 1.47E+04 | 2.70E+02 |
| 0.05% Ag$_2$SO$_4$ | 3.97E+06 | 7.46E+05 | 1.22E+05 |
| 0.05% Ag$_2$SO$_4$ + 10 ppm ZPT | 3.97E+06 | 4.35E+06 | 8.85E+05 |
| 0.5% Ag$_2$SO$_4$ | 3.97E+06 | 1.65E+06 | 1.00E+00 |
| 0.5% Ag$_2$SO$_4$ + 10 ppm ZPT | 3.97E+06 | 2.66E+06 | 1.00E+00 |
| 0.05% MnSO$_4$ | 3.97E+06 | 1.97E+07 | 5.91E+06 |
| 0.05% MnSO$_4$ + 10 ppm ZPT | 3.97E+06 | 3.72E+04 | 4.15E+03 |
| 0.5% MnSO$_4$ | 3.97E+06 | 1.16E+05 | 2.35E+02 |
| 0.5% MnSO$_4$ + 10 ppm ZPT | 3.97E+06 | 2.87E+04 | 5.00E+01 |
| 0.05% BiCl$_3$ | 3.97E+06 | 1.96E+07 | 3.03E+06 |
| 0.05% BiCl$_3$ + 10 ppm ZPT | 3.97E+06 | 1.13E+07 | 1.00E+06 |
| 0.5% BiCl$_3$ | 3.97E+06 | 1.11E+06 | 3.42E+05 |
| 0.5% BiCl$_3$ + 10 ppm ZPT | 3.97E+06 | 4.66E+03 | 1.00E+00 |
| 0.05% Na$_2$SO$_4$ | 3.97E+06 | 3.75E+07 | 3.42E+06 |

TABLE 2(a)-continued

Data for $Mg^{2+}$, $Ag^+$, $Mn^{2+}$, $Bi^{3+}$, $Na^+$

| | Plate Area Colonized (mm2) | | |
| --- | --- | --- | --- |
| | 0 Hours | 24 Hours | 48 Hours |
| 0.05% Na$_2$SO$_4$ + 10 ppm ZPT | 3.97E+06 | 3.43E+05 | 4.70E+03 |
| 0.5% Na$_2$SO$_4$ | 3.97E+06 | 1.44E+07 | 2.95E+06 |
| 0.5% Na$_2$SO$_4$ + 10 ppm ZPT | 3.97E+06 | 1.69E+05 | 3.60E+03 |

TABLE 2(b)

Data for $Zn^{2+}$, $Cu^{2+}$

| | Plate Area Colonized (mm2) | | | |
| --- | --- | --- | --- | --- |
| | 0 Hours | 4 Hours | 24 Hours | 48 Hours |
| Negative Control | 2.12E+07 | 2.44E+08 | 1.51E+08 | 7.00E+08 |
| 10 ppm ZPT | 2.12E+07 | 3.49E+05 | 6.44E+06 | 4.86E+05 |
| 0.05% ZnSO$_4$ | 2.12E+07 | 8.14E+07 | 7.22E+07 | 3.44E+08 |
| 0.05% ZnSO$_4$ + 10 ppm ZPT | 2.12E+07 | 1.83E+07 | 1.20E+06 | 1.39E+05 |
| 0.5% ZnSO$_4$ | 2.12E+07 | 2.21E+07 | 2.69E+06 | 1.86E+05 |
| 0.5% ZnSO$_4$ + 10 ppm ZPT | 2.12E+07 | 1.63E+07 | 3.17E+05 | 1.00E+00 |
| 0.05% CuSO$_4$ | 2.12E+07 | 9.49E+07 | 1.81E+08 | 3.32E+08 |
| 0.05% CuSO$_4$ + 10 ppm ZPT | 2.12E+07 | 2.22E+07 | 1.00E+00 | 1.00E+00 |
| 0.5% CuSO$_4$ | 2.12E+07 | 1.00E+00 | 1.00E+00 | 1.00E+00 |
| 0.5% CuSO$_4$ + 10 ppm ZPT | 2.12E+07 | 1.00E+00 | 1.00E+00 | 1.00E+00 |

Examples 3 through 26

Topical Compositions

The compositions illustrated in Examples 3 through 26 illustrate specific embodiments of the topical anti-microbial compositions of the present invention, but are not intended to be limiting thereof.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components. As used herein, "minors" refers to those optional components such as preservatives, viscosity modifiers, pH modifiers, fragrances, foam boosters, and the like. As is apparent to one of ordinary skill in the art, the selection of these minors will vary depending on the physical and chemical characteristics of the particular ingredients selected to make the present invention as described herein. Other modifications can be undertaken by the skilled artisan without departing from the spirit and scope of this invention. These exemplified embodiments of the anti-microbial shampoo, anti-microbial styling shampoo, anti-microbial conditioner, anti-microbial leave-on tonic, and anti-microbial foot powder compositions of the present invention provide excellent anti-microbial efficacy.

Examples 3-13

Anti-Microbial Shampoo

A suitable method for preparing the anti-microbial shampoo compositions described in Examples 3-13 (below) follows:

ture. Cationic polymer is dispersed in water as an about 0.1% to about 10% aqueous solution and then added to the final mix. Once all components have been added, additional viscosity and pH modifiers may be added, as needed, to the mixture to adjust product viscosity and pH to the extent desired.

| Component | Weight Percent | | | | | |
| --- | --- | --- | --- | --- | --- | --- |
| | Example 3 | Example 4 | Example 5 | Example 6 | Example 7 | Example 8 |
| Ammonium Laureth-3 Sulfate | 9.90 | 9.90 | 9.90 | 9.90 | 9.90 | 6.00 |
| Ammonium Lauryl Sulfate | 6.00 | 6.00 | 6.00 | 6.00 | 6.00 | 10.00 |
| Potassium Hydroxide | 0.86 | 0.86 | 0.86 | 0.86 | 0.86 | 0.86 |
| Citric Acid Anhydrous | 1.84 | 1.84 | 1.84 | 1.84 | 1.84 | 1.84 |
| Ethylene Glycol Distearate | 1.50 | 1.50 | 1.50 | 1.50 | 1.50 | 1.50 |
| Cocamide MEA | 0.80 | 0.80 | 0.80 | 0.80 | 0.80 | 0.80 |
| Cetyl Alcohol | 0.90 | 0.90 | 0.90 | 0.90 | 0.90 | 0.90 |
| Copper Sulfate Pentahydrate | 0.80 | 0.80 | 0.40 | 0.00 | 0.40 | 0.80 |
| Zinc Sulfate | 0.00 | 0.00 | 0.00 | 2.00 | 1.00 | 0.00 |
| Perfume | 0.75 | 0.75 | 0.75 | 0.75 | 0.75 | 0.75 |
| Potassium Hydroxide | 0.33 | 0.33 | 0.33 | 0.33 | 0.33 | 0.33 |
| Sodium Citrate Dihydrate | 0.40 | 0.40 | 0.40 | 0.40 | 0.40 | 0.40 |
| Sodium Benzoate | 0.13 | 0.13 | 0.13 | 0.13 | 0.13 | 0.13 |
| Kathon CG | 0.02 | 0.02 | 0.02 | 0.02 | 0.02 | 0.02 |
| Zinc Pyrithione | 1.00 | 2.00 | 1.00 | 1.00 | 1.00 | 1.00 |
| Water | q.s. | q.s. | q.s. | q.s. | q.s. | q.s. |

| Component | Weight Percent | | | | |
| --- | --- | --- | --- | --- | --- |
| | Example 9 | Example 10 | Example 11 | Example 12 | Example 13 |
| Ammonium Laureth-3 Sulfate | 9.90 | 9.90 | 9.90 | 9.90 | 6.00 |
| Ammonium Lauryl Sulfate | 6.00 | 6.00 | 6.00 | 6.00 | 10.00 |
| Potassium Hydroxide | 0.86 | 0.86 | 0.86 | 0.86 | 0.86 |
| Citric Acid Anhydrous | 1.84 | 1.84 | 1.84 | 1.84 | 1.84 |
| Ethylene Glycol Distearate | 1.50 | 1.50 | 1.50 | 1.50 | 1.50 |
| Cocamide MEA | 0.80 | 0.80 | 0.80 | 0.80 | 0.80 |
| Cetyl Alcohol | 0.90 | 0.90 | 0.90 | 0.90 | 0.90 |
| Copper Sulfate Pentahydrate | 0.80 | 0.80 | 0.40 | 0.00 | 0.80 |
| Zinc Sulfate | 0.00 | 0.00 | 0.00 | 2.00 | 0.00 |
| Perfume | 0.75 | 0.75 | 0.75 | 0.75 | 0.75 |
| Potassium Hydroxide | 0.33 | 0.33 | 0.33 | 0.33 | 0.33 |
| Sodium Citrate Dihydrate | 0.40 | 0.40 | 0.40 | 0.40 | 0.40 |
| Sodium Benzoate | 0.13 | 0.13 | 0.13 | 0.13 | 0.13 |
| Kathon CG | 0.02 | 0.02 | 0.02 | 0.02 | 0.02 |
| Zinc Pyrithione | 0.50 | 1.00 | 0.50 | 1.00 | 1.00 |
| Ketaconazole | 0.50 | 1.00 | 0.50 | 0.50 | 0.50 |
| Water | q.s. | q.s. | q.s. | q.s. | q.s. |

About one-third to all of the ammonium laureth sulfate (added as 25 wt % solution) is added to a jacketed mix tank and heated to about 60° C. to about 80° C. with slow agitation to form a surfactant solution. Cocamide MEA and fatty alcohols, (where applicable), are added to the tank and allowed to disperse. Salts (e.g. potassium chloride) and pH modifiers (e.g. citric acid, sodium citrate) are added to the tank and allowed to disperse. Ethylene glycol distearate ("EGDS") is added to the mixing vessel and allowed to melt. After the EGDS is melted and dispersed, preservative is added to the surfactant solution. The resulting mixture is cooled to about 25° C. to about 40° C. and collected in a finishing tank. As a result of this cooling step, the EGDS crystallizes to form a crystalline network in the product. The remainder of the ammonium laureth sulfate and other components, including the silicone and anti-microbial agent(s), are added to the finishing tank with agitation to ensure a homogeneous mix-

Examples 14-17

Anti-Microbial Styling Shampoo

A suitable method for preparing the anti-microbial styling shampoo compositions described in Examples 14-17 (below) by conventional formulation and mixing techniques follows:

The hair styling polymer should first be dissolved in the volatile carrier. The anti-microbial active is then added to this styling polymer/volatile carrier premix. The styling polymer/volatile carrier/anti-microbial active premix may then be added to a premix of the surfactants, or some portion of the surfactants, and the solid components which has been heated to melt the solid components, e.g., about 87° C. This mixture is then pumped through a high shear mill and cooled, and then the remaining components are mixed in. Alternatively, the styling polymer/volatile carrier/anti-microbial active premix may be added to this final mix, after cooling. The composition should have a final viscosity of from about 2000 to about 12,000 cps. The viscosity of the composition can be adjusted using sodium chloride or ammonium xylenesulfonate as needed.

cially anti-dandruff, efficacy, while not deteriorating conditioning benefits such as wet hair feel, spreadability, and rinsability, as well as providing glossiness, and dry combing.

| | Weight Percent | | | |
|---|---|---|---|---|
| Component | Example 14 | Example 15 | Example 16 | Example 17 |
| Ammonium Laureth-3 Sulfate | 9.00 | 9.00 | 9.00 | 6.00 |
| Ammonium Lauryl Sulfate | 3.00 | 3.00 | 3.00 | 6.00 |
| Perfume | 0.85 | 0.85 | 0.85 | 0.85 |
| PEG-14M | 0.30 | 0.30 | 0.30 | 0.30 |
| Guar Hydroxypropyltrimonium Chloride (2) | 0.15 | 0.15 | 0.15 | 0.15 |
| Sodium Lauroamphoacetate | 5.08 | 5.08 | 5.08 | 5.08 |
| Zinc Pyrithione | 1.00 | 1.00 | 1.00 | 1.00 |
| Dihydrogenated Tallowamidoethyl Hydroxyethylmonium Methosulfate (1) | 1.00 | 1.00 | 1.00 | 1.00 |
| TBA/EHM Polymer in Isohexadecane | 2.70 | 2.70 | 2.70 | 2.70 |
| C10-11 Isoparaffin | 1.33 | 1.33 | 1.33 | 1.33 |
| Citric Acid Anhydrous | 0.83 | 0.83 | 0.83 | 0.83 |
| Ethylene Glycol Distearate | 0.57 | 0.57 | 0.57 | 0.57 |
| Sodium Chloride | 0.45 | 0.45 | 0.45 | 0.45 |
| Dimethicone | 0.25 | 0.25 | 0.25 | 0.25 |
| Copper Sulfate Pentahydrate | 0.80 | 0.00 | 0.40 | 0.40 |
| Zinc Sulfate | 0.00 | 2.00 | 1.00 | 0.00 |
| Polyquaternium-10 | 0.15 | 0.15 | 0.15 | 0.15 |
| Trihydroxystearin | 0.15 | 0.15 | 0.15 | 0.15 |
| Panthenol | 0.05 | 0.05 | 0.05 | 0.05 |
| Pantyl Ethyl Ether | 0.05 | 0.05 | 0.05 | 0.05 |
| Water | q.s. | q.s. | q.s. | q.s. |

(1) Available under the tradename Varisoft 110 from Sherex Chemical Co. (Dublin, Ohio, USA)
(2) Available under the tradename Jaguar C-17 from Rhone-Poulenc. (Cranbury, New Jersey, USA)

Examples 18-21

Hair Conditioning Composition

A suitable method for preparing the anti-microbial hair conditioning compositions described in Examples 18-21 (below) by conventional formulation and mixing techniques follows:

When included in the composition, polymeric materials such as polypropylene glycol are dispersed in water at room temperature to make a polymer solution, and heated up to above 70° C. Amidoamine and acid, and when present, other cationic surfactants, ester oil of low melting point oil are added in the solution with agitation. Then high melting point fatty compound, and when present, other low melting point oils and benzyl alcohol are also added in the solution with agitation. The mixture thus obtained is cooled down to below 60° C., and the remaining components such as zinc pyrithione, metal ion source, and silicone compound are added with agitation, and further cooled down to about 30° C.

A triblender and/or mill can be used in each step, if necessary to disperse the materials. Alternatively, up to 50% of the acid can be added after cooling below 60° C.

The embodiments disclosed herein have many advantages. For example, they can provide effective anti-microbial, espe-

| | Weight Percent | | | |
|---|---|---|---|---|
| Component | Example 18 | Example 19 | Example 20 | Example 21 |
| Cyclopentasiloxane | 3.57 | 3.57 | 3.57 | 3.57 |
| Stearamidopropyl Dimethylamine | 1.00 | 1.00 | 1.00 | 1.00 |
| Zinc Pyrithione | 1.00 | 0.50 | 1.00 | 0.50 |
| Panthenol | 0.03 | 0.03 | 0.03 | 0.03 |
| Panthenyl Ethyl Ether | 0.23 | 0.23 | 0.23 | 0.23 |
| Cetyl Alcohol | 0.96 | 0.96 | 0.96 | 0.96 |
| Quaternium-18 | 0.75 | 0.75 | 0.75 | 0.75 |
| Stearyl Alcohol | 0.64 | 0.64 | 0.64 | 0.64 |
| Dimethicone | 0.63 | 0.63 | 0.63 | 0.63 |
| PEG-2M | 0.50 | 0.50 | 0.50 | 0.50 |
| Copper Sulfate Pentahydrate | 0.80 | 0.00 | 0.40 | 0.40 |
| Zinc Sulfate | 0.00 | 2.00 | 1.00 | 0.00 |
| Polysorbate 60 | 0.50 | 0.50 | 0.50 | 0.50 |
| Cetearyl Alchol | 0.50 | 0.50 | 0.50 | 0.50 |
| Benzyl Alcohol | 0.40 | 0.40 | 0.40 | 0.40 |
| Oleyl Alcohol | 0.25 | 0.25 | 0.25 | 0.25 |
| Glyceryl Stearate | 0.25 | 0.25 | 0.25 | 0.25 |
| Hydroxyethylcellulose | 0.25 | 0.25 | 0.25 | 0.25 |
| Perfume | 0.25 | 0.25 | 0.25 | 0.25 |
| Citric Acid | 0.13 | 0.13 | 0.13 | 0.13 |
| EDTA | 0.10 | 0.10 | 0.10 | 0.10 |
| Niacinamide | 0.05 | 0.05 | 0.05 | 0.05 |
| Water | q.s. | q.s. | q.s. | q.s. |

Examples 22-25

Anti-Microbial Leave-In Hair Tonic

A suitable method for preparing the anti-microbial leave-in hair tonic compositions described in Examples 22-25 (below) follows:

Add most of the formula water; with stirring, add carbomer and mix until fully dispersed. In a separate vessel, add ethanol and then molten PEG-60 hydrogenated castor oil and perfume. Transfer this to main mix tank with agitation. Add other water soluble ingredients, minors, zinc pyrithione and metal salts. Slowly add styryl silicone and let stir. Add triethanolamine slowly with stirring.

| | Weight Percent | | | |
|---|---|---|---|---|
| Component | Example 22 | Example 23 | Example 24 | Example 25 |
| Carbomer | 0.50 | 0.50 | 0.50 | 0.50 |
| Triethanolamine | 0.30 | 0.30 | 0.30 | 0.30 |
| Ethanol | 25.00 | 25.00 | 25.00 | 25.00 |
| Zinc Pyrithione | 0.10 | 0.10 | 0.10 | 0.10 |
| Camphor | 0.05 | 0.05 | 0.05 | 0.05 |
| Menthol | 0.50 | 0.50 | 0.50 | 0.50 |
| Panthenol | 0.05 | 0.05 | 0.05 | 0.05 |
| Pantyl Ethyl Ether | 0.05 | 0.05 | 0.05 | 0.05 |
| Copper Sulfate Pentahydrate | 0.08 | 0.00 | 0.04 | 0.08 |
| Zinc Sulfate | 0.00 | 0.20 | 0.20 | 0.20 |
| Lactic Acid | 0.05 | 0.05 | 0.05 | 0.05 |
| Styryl Silicone | 0.50 | 0.50 | 0.50 | 0.50 |
| Ceteareth-20 | 0.15 | 0.15 | 0.15 | 0.15 |
| PEG-60 Hydrogenated Castor Oil | 0.15 | 0.15 | 0.15 | 0.15 |

-continued

| Component | Weight Percent | | | |
|---|---|---|---|---|
| | Example 22 | Example 23 | Example 24 | Example 25 |
| Perfume | 0.50 | 0.50 | 0.50 | 0.50 |
| Water | q.s. | q.s. | q.s. | q.s. |

Example 26

5 Anti-microbial Foot Powder

The foot powder composition of Example 26 is prepared by thoroughly mixing the ingredients in a mixing vessel. The powder may then be ground and/or sifted if necessary.

| Component | Weight Percent |
|---|---|
| Talc | 73.25% |
| Calcium Propionate | 15.0 |
| Zinc Propionate | 5.0 |
| Zinc Caprylate | 5.0 |
| Propionic Acid | 0.25 |
| Zinc Sulfate | 0.50 |
| Zinc Pyrithione | 1.0 |
| | 100.00 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A topical composition for treating microbes, in order to inhibit the growth on the skin or scalp of said microbes, comprising:
    a) from about 0.001% to about 2%, by weight of the composition, of an anti-microbial active selected from the group consisting of polyvalent metal salts of pyrithione;
    b) from about 0.001% to about 10%, by weight of the composition, of a metal ion source selected from group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, colloidal silver, silver bromide, silver chloride, silver citrate, silver iodide, silver lactate, silver nitrate, silver oxide, silver picrate, and mixtures thereof; and
    c) a topical carrier for the anti-microbial active and the metal salt; wherein the weight ratio of the metal source to the anti-microbial active is from about 5:100 to about 5:1 and wherein at least 50% of the anti-microbial active is insoluble in the composition.

2. A topical composition according to claim 1, wherein the polyvalent metal salt of pyrithione is selected from the group consisting of magnesium pyrithione, barium pyrithione, bismuth pyrithione, strontium pyrithione, copper pyrithione, zinc pyrithione, cadmium pyrithione, zirconium pyrithione and mixtures thereof.

3. A topical composition according to claim 2, wherein the polyvalent metal salt of pyrithione is selected from the group consisting of zinc pyrithione, copper pyrithione, and mixtures thereof.

4. A topical composition according to claim 3, wherein the polyvalent metal salt of pyrithione is zinc pyrithione.

5. A topical composition according to claim 1, wherein the composition is free from strong chelating agents selected from the group consisting of di- or polyamines, diethylene triamine penta-acetic acid, tetraethylene triamine, ethylene diamine, diethylene triamine or salts thereof or mixtures thereof.

6. A topical composition according to claim 1, wherein at least 99.99% of the anti-microbial active is insoluble in the composition.

7. A topical composition according to claim 1, wherein 100% of the anti-microbial active is insoluble in the composition.

8. A topical composition according to claim 1, wherein less than 50% of the polyvalent metal salt disassociates into free pyrithione ion in the composition.

9. A topical composition according to claim 8, wherein less than 5% of the polyvalent metal salt disassociates into free pyrithione ion in the composition.

10. A topical composition for treating microbes, in order to inhibit the growth on the skin or scalp of said microbes, comprising:
    a) from about 0.001% to about 2%, by weight of the composition, of an anti-microbial active selected from the group consisting of polyvalent metal salts of pyrithione;
    b) from about 0.001% to about 10%, by weight of the composition, of a metal ion source selected from group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, copper sulfate, and mixtures thereof; and
    c) a topical carrier for the anti-microbial active and the metal salt; wherein the weight ratio of the metal source to the anti-microbial active is from about 5:100 to about 5:1 and wherein at least 50% of the anti-microbial active is insoluble in the composition.

11. A topical composition according to claim 10, wherein the composition comprises from about 0.1% to about 2%, by weight of the composition, of the metal ion source.

12. A topical composition according to claim 10, wherein the metal ion source is selected from the group consisting of soluble copper salts.

13. A topical composition according to claim 12, wherein the metal ion source is copper sulfate.

14. A topical composition for treating microbes, in order to inhibit the growth on the skin or scalp of said microbes, comprising:
    a) from about 0.001% to about 2%, by weight of the composition, of an anti-microbial active selected from the group consisting of polyvalent metal salts of pyrithione;
    b) from about 0.001% to about 10%, by weight of the composition, of a metal ion source selected from group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, copper sulfate, colloidal silver, silver bromide, silver chloride, silver citrate, silver iodide, silver lactate, silver nitrate, silver oxide, silver picrate, nickel salts, cadmium salts, mercury salts, and mixtures thereof; and c) a topical carrier for the anti-microbial active and the metal salt;

wherein the weight ratio of the metal source to the anti-microbial active is from about 5:100 to about 5:1 and wherein at least 50% of the anti-microbial active is insoluble in the composition; and wherein the composition further comprises a polyalkylene glycol.

15. A topical anti-microbial composition prepared by the process of mixing:

a) from about 0.1% to about 2%, by weight of the composition, of an anti-microbial active selected from the group consisting of polyvalent metal salts of pyrithione;

b) from about 0.01% to about 5%, by weight of the composition, of a metal ion source selected from group consisting of copper disodium citrate, copper triethanolamine, copper carbonate, cuprous ammonium carbonate, cupric hydroxide, copper chloride, cupric chloride, copper ethylenediamine complex, copper oxychloride, copper oxychloride sulfate, cuprous oxide, copper thiocyanate, copper sulfate, colloidal silver, silver bromide, silver chloride, silver citrate, silver iodide, silver lactate, silver nitrate, silver oxide, silver picrate, nickel salts, cadmium salts, mercury salts, bismuth salts, and mixtures thereof; and c) a topical carrier for the anti-microbial active and the metal salt;

wherein the polyvalent metal salt is zinc pyrithione and the metal ion source is selected from the group consisting of copper salts; and wherein the weight ratio of the metal source to the anti-microbial active is from about 5:100 to about 5:1 and wherein at least 50% of the anti-microbial active is insoluble in the composition.

16. A topical anti-microbial composition according to claim 15 wherein at least 99.9% of the anti-microbial active is insoluble in the composition.

* * * * *